United States Patent
Warburton et al.

(10) Patent No.: US 6,590,957 B1
(45) Date of Patent: Jul. 8, 2003

(54) METHOD AND APPARATUS FOR PRODUCING SPECTRA CORRECTED FOR DEADTIME LOSSES IN SPECTROSCOPY SYSTEMS OPERATING UNDER VARIABLE INPUT RATE CONDITIONS

(75) Inventors: William K. Warburton, 1300 Mills St., Menlo Park, CA (US) 94025; Michael Momayezi, Oakland, CA (US); Peter M. Grudberg, Castro Valley, CA (US); Jackson T. Harris, Berkeley, CA (US)

(73) Assignee: William K. Warburton, Menlo Park, CA (US)

( * ) Notice: Subject to any disclaimer, the term of this patent is extended or adjusted under 35 U.S.C. 154(b) by 0 days.

(21) Appl. No.: 10/099,343

(22) Filed: Mar. 13, 2002

(51) Int. Cl.⁷ ............................. H05G 1/08; A61B 6/00
(52) U.S. Cl. ............................................ 378/91; 378/5
(58) Field of Search ................................ 378/5, 62, 91, 378/901

(56) References Cited

U.S. PATENT DOCUMENTS

| | | | |
|---|---|---|---|
| 4,476,384 A | 10/1984 | Westphal | |
| 5,684,850 A | 11/1997 | Warburton et al. | |
| 5,774,522 A | * 6/1998 | Warburton | ............. 378/91 |
| 5,870,051 A | 2/1999 | Warburton et al. | |
| 5,873,054 A | 2/1999 | Warburton et al. | |
| 6,327,549 B1 | 12/2001 | Bingham et al. | |

OTHER PUBLICATIONS

Harms, J., "Automatic Dead–Time correction for Multichannel, Pulse–height Analyzers at Variable counting Rates," *Nuclear Instruments & Methods*, 53 (1967) pp. 192–196.

Masters et al., "An Investigation into the Harms Dead Time Correction Procedure for Pulse Height Analyzers Using Monte Carlo Modeling Techniques," *IEEE Trans. Nuclear Science*, 17 (1970) pp. 383–389.

Jenkins et al., "Quantitative X–ray Spectrometry" (Marcel Dekker, New York, 1981), Chapter 4, pp. 208–291 (Sections 5 to 8).

Knoll 1989: "Radiation Detection and Measurement," 2nd Ed. by Glenn F. Knoll (J. Wiley, New York, 1989), Chapter 4, Section VII, "Dead Time" pp. 120–128.

Knoll 1989: "Radiation Detection and Measurement," 2nd Ed. by Glenn F. Knoll (J. Wiley, New York, 1989), Chapter 16, Section III, "Pulse Shaping" pp. 564–582.

Upp et al. "An Innovative Method for Dead Time Correction in Nuclear Spectroscopy", Preprint of poster at (Marc V, Honolulu, HI, Apr. 9–14, 2000) pp. 1–13.

X–ray Instrumentation Associates: Application Note 970323–1—"Pileup Inspection and Deadtime in the DXP–4C" pp. 1–4.

\* cited by examiner

*Primary Examiner*—David V. Bruce
(74) *Attorney, Agent, or Firm*—Townsend and Townsend and Crew LLP

(57) ABSTRACT

For pulse processing spectrometers that use a fast channel to detect input pulses, a slow channel to measure the pulses' energies, pileup inspection circuitry pulses, and binning to produce an output spectrum of captured energy values, the correction technique extends the Harms method to produce an estimate <C> of the average ratio of the number of input pulses detected in the fast channel per non-piled-up pulse whose captured energy value is to be binned into the output spectrum and, for each such non-piled-up pulse, adding the value <C> to the corrected output spectrum in the bin dictated by the captured energy value. The uncorrected spectrum is formed in the traditional manner by simply adding 1 to the equivalent bin. Three techniques are disclosed for producing the estimate <C>, a running average, a bucket averaging, and a circular buffer method.

36 Claims, 9 Drawing Sheets

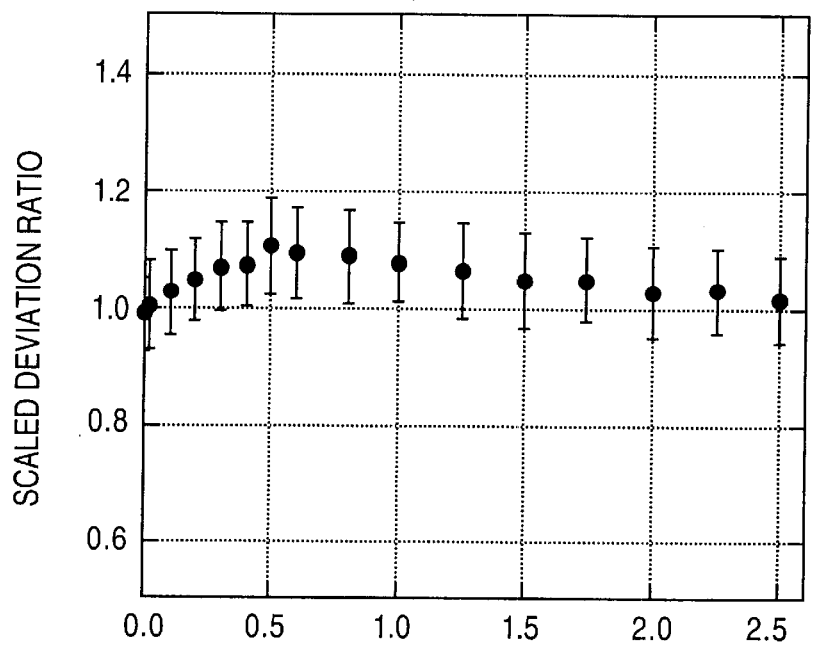
FIG. 7  $\rho$ = ICR * DEADTIME
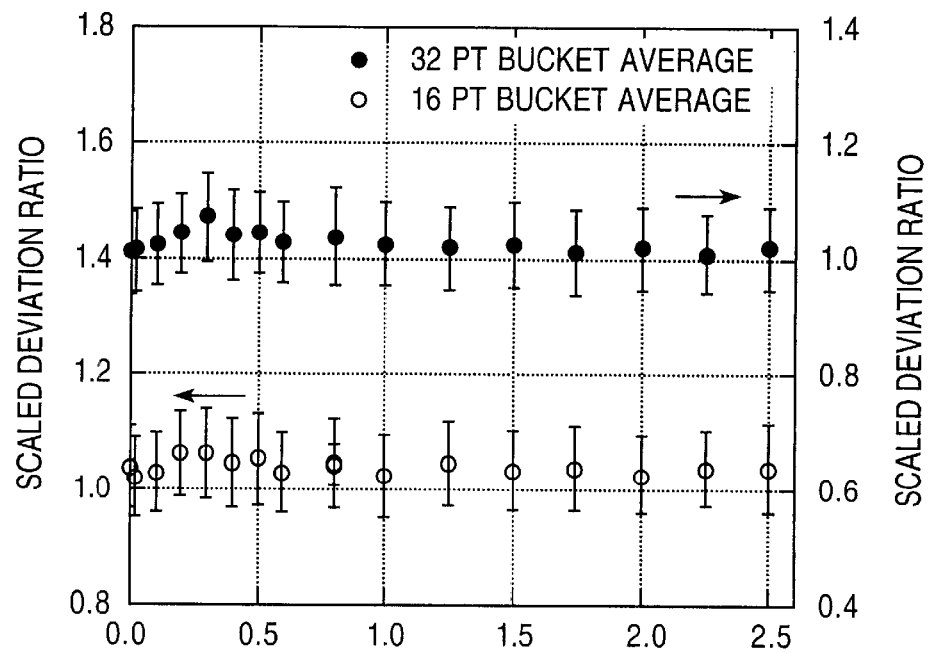
FIG. 9  $\rho$ = ICR * DEADTIME

METHOD AND APPARATUS FOR PRODUCING SPECTRA CORRECTED FOR DEADTIME LOSSES IN SPECTROSCOPY SYSTEMS OPERATING UNDER VARIABLE INPUT RATE CONDITIONS

BACKGROUND OF THE INVENTION

The present invention relates generally to systems for detecting, counting and measuring signal events produced by preamplifiers connected to radiation detectors used to detect x-rays, gamma-rays, nuclear particles, and the like. More particularly, it relates to increasing the accuracy with which the energy spectra of these events can be obtained under conditions of varying input counting rate by increasing the accuracy of determining the number of events that are lost due to pileup in the spectrometer's energy filter. The specific embodiment described relates to a spectrometer used with a solid state detector, but the same techniques apply to radiation spectrometers operating with other detectors as well, since the issues relating to pileup are essentially independent of detector type.

A Synopsis of Current Spectrometer Art

FIG. 1 is a schematic diagram of a prior art radiation spectroscopy system employed with a solid state detector diode 7. Similar systems are used for measuring x-ray, gamma-ray and alpha and beta particle radiations, differing primarily in the physical form of the detector diode 7, which might also be replaced with a proportional counter or other detector. All of these detectors 7 share the common property that, when biased by a voltage supply 8, they produce an output current pulse when detecting an absorption event and the total charge $Q_E$ in this pulse is approximately proportional to the energy E of the absorbed ray or particle. This current flows into a preamplifier 10, where it is integrated onto feedback capacitor 13 by amplifier 12, whose output is then a step of amplitude $A_e = Q_E/C_f$, where $C_f$ is the capacitance of feedback capacitor 13. As a matter of nomenclature, pulses produced by the preamplifier in response to radiation absorption events and subsequently processed by the spectroscopy amplifier will often also be referred to as "counts" since the goal of spectroscopic processing is to place them finally as counts in an output spectrum. In common parlance, the two terms are used nearly interchangeably except when the specific nature of one or the other needs to be emphasized.

A spectroscopy amplifier 15 is then used to measure $A_E$. Within modern spectroscopy amplifiers 15 the output 14 of preamplifier 10 is commonly sent to both a "slow" energy filter circuit 17, which produces a low noise, shaped output pulse on line 19 whose peak height is proportional to $A_E$, and to a pileup inspection circuit 18, which inspects for the presence of signal steps (events) and signals the filter peak capture circuit 20 via signal line 22 to capture the amplitudes of shaped pulses from the energy filter circuit 17 which are sufficiently separated in time so that they do not interfere with each other's amplitudes (i.e., do not "pile up"). The inspection circuit 18 also determines when events are sufficiently separated so that the output of the energy filter circuit has returned to its DC value and signals the baseline capture circuit 24 using signal line 25 to capture these values so that they may be subtracted from captured peak values by the subtraction circuit 28. These differences are then passed to a multichannel analyzer (MCA) or digital signal processor (DSP) 29, for binning to form a spectral representation (spectrum) of the energy values present in the incident radiation.

Details of the pileup inspection circuit 18 are shown in FIG. 2. This circuit typically (see, for example, U.S. Pat. No. 5,873,054, issued to W. K. Warburton and Z. Zhou [WARBURTON 1999B], for a digital implementation) consists of a "fast" filter circuit 30, whose filter time constant is ideally an order of magnitude or more shorter than that of the energy filter circuit 17. The fast filter's output 31 connects to a threshold comparator 32, whose output 35 connects to a block of timing and logic circuitry 36. The comparator compares the output 31 of the fast filter 30 to a threshold level T 37 and outputs a logic level 1 to timing and logic block 36 whenever the former exceeds the latter. The timing and logic block then uses this information to determine when valid energy filter peaks and baselines may be captured.

Pileup

FIG. 3 shows the origin of counting losses in radiation spectrometers of the type described above. Trace 40 represents the voltage output 14 from the preamplifier 10, with the steps A–E occurring in response to five radiation events. Trace 42 represents the output 31 of fast filter 30, which produces a shaped pulse (e.g., 44) in response to an input event pulse (e.g., A). Trace 46 shows the output 35 of the comparator, which is unity whenever the fast filter output 31 exceeds threshold T 37. Trace 48 shows the ideal output (i.e., impulse function) of the energy filter 17 for each input event pulse. In the example shown, which is typical for a digital spectrometer, this impulse function is a trapezoidal voltage signal having a peaking time $t_p$ and a gap time $t_g$. Since the energy filter is a linear device, its output, trace 50 is the sum of the impulse functions generated for the individual steps. For the case of an event pulse (e.g., A) which is well isolated from its neighbors in time, the energy filter output is identical to the impulse function and its peak amplitude $V_A$, which is proportional to the energy of the event, can be reliably captured at a time $t_c$ after the comparator output 46 goes high. If, however, the step pulses are too close together, as is the case for steps B and C, their impulse functions "pile up" on each other 52, distorting the peaks of both so that neither $V_B$ nor $V_C$ can be recovered. In the present example, this occurs when they are closer together than the sum of the times $t_p$ and $t_g$. The job of the timing and logic block 36, therefore, is to measure the time between consecutive pulses and not enable the peak capture circuit 20 for any pulse that piles up with either its preceding or following nearest neighbor in time. Most modern spectrometer designs implement this function, with the result that these pulses are not placed in the output spectrum and are thereby "lost" to pileup. This situation is accepted as the lesser of two evils since, if the distorted pulse amplitude were captured and included in the spectrum it would be placed at an incorrect energy location corresponding to the energy of neither of its component pulses and, in addition, the number of counts in the spectrum would still be in error by one count.

The net result is that, for a given input count rate ICR, the rate OCR at which counts are placed into the spectrum is given by the well known deadtime formula:

$$OCR = ICR \exp(-ICR\tau_d) \qquad (1)$$

where $\tau_d$ is the spectrometer's deadtime. In the digital spectrometer case being described, $\tau_d$ is approximately equal to $2(t_p + t_g)$. The maximum OCR occurs at $ICR_{max} = \tau_d^{-1}$ and is given by $OCR_{max} = ICR_{max}/e = (e\tau_d)^{-1}$, at which point $(1 - e^{-1}) = 63\%$ of all counts are lost to pileup. At higher ICR values even more counts are lost. The reference books by Jenkins et al. and Knoll provide further information on the subject of deadtime [JENKINS 1981, KNOLL 1989].

At very high data rates, the more difficult case represented by steps D and E in trace 40 also begins to occur frequently. These pulses are sufficiently close together that the fast filter output 42 does not fall below the threshold T 37 between them. Their impulse functions nearly superimpose and the energy filter output 54 looks nearly identical to the output from a valid, well isolated single pulse. This "fast channel pileup" may or may not be detected, depending upon the time separation between the two events and the sophistication of the spectrometer. One approach to minimizing fast channel pileup events in the output spectrum (see WARBURTON 1999B) is to compare the time $t_f$ 56 that the fast channel spends above threshold to the value for a well isolated event and to also exclude from the spectrum those pulses that are excessively long.

The number of counts lost to fast pileup can readily become large compared to estimated counting statistics errors. For example, for a fast channel deadtime of 0.5 $\mu$s, a common pulse-pair resolution, at 100 kcps ICR, almost 5% of all counts are lost to fast pileup, whereas only 10,000 counts need be collected in an MCA channel to obtain 1% statistical accuracy. Since the same loss rate affects the entire spectrum, this does not affect measurements relying on the relative amplitudes of the spectral peaks. It does, however, directly affect any attempts at absolute activity measurement.

Correcting for Pileup Losses

For many qualitative measurements, an undistorted spectrum is all that is required. In quantitative measurements, however, both an accurate spectrum and an accurate ICR measurement are required. Various methods have been developed to treat this problem when the ICR is constant during the course of the measurement, and these are well covered by Jenkins et al. [JENKINS 1981]. The methods include: 1) extending the measurement's livetime by the use of live-time clocks; 2) adding a test pulser of known rate to the input signal; or 3) extracting an ICR measurement from the fast filter and then producing a deadtime corrected spectrum by scaling the uncorrected output spectrum by the ratio of ICR/OCR. [XIA 1997] In this latter, non-livetime-extending method, the event pulses detected in the fast filter output 31 by the threshold comparator circuit 32 are counted while the spectrum is collected. At the end of the collection time t the number of counts $N_s$ in the spectrum is t*OCR, while the number of pulses $N_f$ counted from the fast filter output is a good measure of t*ICR, excluding fast channel pileup. If the values in the uncorrected output spectrum are then scaled by the ratio $<C>=N_f/N_s$, the corrected output spectrum will contain the correct number of counts t*ICR. The ratio $<C>$ is then a measure over the entire counting period of the average number of input counts per captured, un-piled-up output count. If the fast channel deadtime $\tau_{df}$ is measured, $<C>$ can also be corrected for fast channel pileup losses by correcting ICR appropriately.

For the purposes of fitting and analyzing the spectra, it is also useful to be able to estimate the standard deviations of the counts recorded in their bins. In the case of livetime-extending counting methods, the standard deviation of the counts in any MCA bin is just the square root of the number of counts in that bin. In the non-livetime-extending methods, $<C>=N_f/N_s$ scaling method, the standard deviation $\sigma_{ci}$ of the counts $N_{ci}$ in bin i of the corrected spectrum is given by $$\sigma_{ci}=<C>\sigma_{ui}, \quad (2a)$$

where $$<C>=(N_f/N_s)=N_{ci}/N_{ui}, \text{ and } \sigma_{ui}=\text{sqrt}(N_{ui}) \quad (2b)$$

so that $$\sigma_{ci}=(N_{ci}/N_{ui})\text{sqrt}(N_{ui})=N_{ci}/\text{sqrt}(N_{ui}), \quad (2c)$$

where the standard deviation $\sigma_{ui}$ in bin i of the uncorrected spectrum equals the square root of $N_{ui}$, the counts in bin i of the uncorrected spectrum. We are able to equate $N_{ci}/N_{ui}$ with $N_f/N_s$ because the same scaling factor is used for all bins in the spectra. In general, the counting statistics in the non-livetime-extending case are not as good as in the livetime-extending methods because the overall counting times are shorter by the ratio OCR/ICR. If equal real counting times are employed, the two methods produce identical counting statistics.

The Time-Varying Spectrum Problem

Many significant problems, however, involve counting under situations where the ICR varies significantly, and often rapidly, in time. Examples include scanning x-ray mapping, neutron activation analysis, and effluent monitoring where the occasional "hot particle" may pass by the monitoring station. In these situations, it is desirable, although difficult, to recover accurate estimates of both the instantaneous ICR and the measurements' statistical uncertainties for use in analytical computations.

All of the above deadtime correction methods are based on the assumption that ICR is constant in time. When this assumption breaks down, so do the methods. This is easily shown by a simple numerical example. Suppose that a 10 second live counting time t is requested and that, unknown to the detector operator, during the first second a "hot" source A of $ICR_A$ is near the detector so that it experiences 90% dead time. After 1 second this source is replaced by a "cool" source B of $ICR_B$ that only produces 10% deadtime in the detector. During the first 1 second of real time only 0.1 seconds of livetime are recorded, while 9.9 seconds of livetime are recorded during the next 11 seconds. Thus the counter counts for 12 seconds to achieve 10 seconds of livetime. In the collected composite spectrum, the ratio of the A spectrum counts to the B spectrum counts is 0.1 $ICR_A$ to 9.9 $ICR_B$, since all the livetime extension occurred while the cool source was present. This represents a gross distortion of the fact that, during the measurement, the detector was actually exposed to 1*$ICR_A$ plus 11*$ICR_B$ counts.

From this example, it is clear that, if count rates are time varying, then corrections for lost counts must be made in real time if they are to accurately report the counts to which the detector is exposed. As the example shows, this becomes critically important when the features of the spectrum are evolving rapidly in time.

Jenkins et al. report only a single method, due to Harms [HARMS 1967], that has this feature. In the Harms method, the output of the threshold comparator 32 is taken as the true ICR and fed into an ICR scaler. Each time the pileup inspector 18 detects a good peak, so that the output of the filter peak capture circuit 20 is sent to the MCA 29 for binning, the number in the ICR scaler is placed in that bin instead and the ICR scaler zeroed. Thus all detected ICR counts are placed into the spectrum and, on average, all spectral features are correctly recovered. While the variance of the number of counts placed into the whole spectrum is correctly represented by the number of counts in the spectrum, Harms did not show, and Jenkins doubts, that the variance of the number of counts in any MCA bin is correctly given by the number of counts in that bin. That is, the recovered spectrum in the MCA cannot be effectively used in an analysis program because the statistical accuracy of the counts in each of its bins is unknown (in contrast to the usual spectrum, where the variance of the counts in a bin is equal to that number of counts).

Since Jenkins' review, Westphal has presented a method (see U.S. Pat. No. 4,476,384, issued to G. P. Westphal [WESTPHAL 1984]), for a real time method for correcting for pileup losses. Westphal works with the output of the energy filter, comparing it to a threshold in a manner similar to livetime inspectors. For each pulse detected he generates a logic signal that is HI for both the time above threshold plus an extension to accommodate leading edge pileup. Then, over a fixed interval, he counts the number of cycles of a timing clock that occur while his logic signal is LO and compares this number to the total number of clock cycles during the same interval. The ratio of total cycles to counted cycles is a measure of the ratio of real time to livetime and this ratio, as a "number of counts," is added each time a good pulse is placed into an MCA channel. The test interval employed can be quite short, in the millisecond regime, so that this approach is fully capable of handling rapid spectral evolution of the type seen in neutron activation analysis, for example. This approach has two weaknesses: first that the precision of the measurement is limited by the clock frequency, and, second and more significantly, that, as in the Harms method, there is no estimate produced of the statistical significance of the numbers recorded in the final MCA spectrum.

Recently, Bingham et al. (see U.S. Pat. No. 6,327,549, issued to R. D. Bingham et al. [BINGHAM 2000]) presented a method that both makes corrections in real time and also produces variance estimates for the numbers in the recorded MCA spectrum. This method uses an accurate Gedcke-Hale livetime clock to measure the ratio r of realtime to livetime over short time intervals. Then, each time a good pulse is detected, r is added to a corrected MCA spectrum at the pulse's energy value. In addition, a "variance spectrum" is also generated by adding the value $r^2$ into a second spectrum at the same location. The authors present a mathematical argument to show that, when data collection is complete, the variance of the counts in each channel in the r corrected spectrum is given by the number of counts collected in the same channel in the $r^2$ variance spectrum. The advantages claimed for this method are that no manual setup steps or calibrations are required, that variances on the counts are produced, and that the corrections are reasonably accurate. Limitations include the known accuracy limitations of the Gedcke-Hale livetime clock [Jenkins 1981], the requirement for the $r^2$ calculations, which may limit throughput at very high data rates, and, from the authors' published data, the inability of the system to accurately recover the counts from a fixed intensity source in the presence of a rate adjusting source at 80–90% dead time [UPP 2000 ].

SUMMARY OF THE INVENTION

The present invention extends the method of Harms in a manner that not only produces effectively loss-free output spectra but also generates the statistical uncertainty of the values in the deadtime-corrected output spectrum without additional computation. By further correcting for pileup losses in the fast event-detection filter circuit, it becomes possible to achieve very high accuracy, even at deadtimes exceeding 90%.

In brief, the approach entails producing from time to time an estimate <C> of the average ratio of the number of input pulses detected in the fast channel per non-piled-up "good" pulse whose captured energy value is to be binned in the output spectrum, and, for each such non-piled-up pulse, adding the value <C> into the output spectrum in the bin dictated by the pulse's captured energy value, thereby producing an output spectrum corrected for pileup losses. We also preferably save an uncorrected spectrum that is formed in the present method by adding 1 to the same bin in the uncorrected spectrum as the bin to which <C> is added in the corrected spectrum. This is just the spectrum that is traditionally saved in time-invariant measurements. By the use of Monte Carlo modeling we have determined that, when <C> is produced in accordance with the invention, standard deviations of counts in any bin in the corrected spectrum can be accurately estimated by scaling the standard deviation of the counts in the same bin in the uncorrected spectrum by the ratio of their counts. That is, the standard deviation $\sigma_{ci}$ in the counts $N_{ci}$ in the $i^{th}$ bin of the corrected spectrum is given by $$\sigma_{ci}=\text{sqrt}(N_{ui})(N_{ci}/N_{ui})=N_{ci}/\text{sqrt}(N_{ui}) \qquad (3)$$

where $N_{ui}$ is the number of counts in the $i^{th}$ bin of the uncorrected spectrum. Thus, provided that <C> is produced according to the methods we disclose, we can estimate the standard deviations $\sigma_{ci}$ using exactly the same prior art method already used in the case of non-livetime extending spectroscopy per Eqns. 2a–2c.

While the use of the uncorrected spectrum to estimate the standard deviations in the corrected spectrum is, per se, prior art, an important difference must be recognized. The inventive distinction between the present method and the prior art non-livetime-extended method lies in the method by which the corrected spectrum is collected. In the case of static ICRs, which is the provenance of the non-livetime-extended method, <C> is a constant which can be determined following data collection (i.e., as the ratio <C>=$N_f/N_s$=ICR/OCR). The present invention, however, determines <C> dynamically as the counting proceeds, and is able to deal with cases where ICR, and therefore <C>, may vary as a function of time. Once a spectrum has been acquired, however, then the same method, represented by Eqns. 2a–2c, can be used in both cases to accurately estimate the standard deviations of the counts in its channels. Viewed another way, in the non-livetime-extending method, <C> is computed over the entire counting time and the entire collected spectrum scaled once, at the end. In the present case, we disclose methods by which <C> may be computed in real time and the corrected spectrum "scaled" on a count-by-count basis in such a way that Eqns. 2a–2c remain true. This achievement is nontrivial and earlier methods (e.g., Harms) were unable to attain it.

In particular, our modeling shows that, when <C> is not optimally formed, $\sigma_{ci}$ will be larger than the value given by Eqns. 2a–2c, which therefore represent the ideal result, namely the minimum standard deviation that can be achieved. That is, the minimum statistical fluctuations that can be obtained are those of the uncorrected spectrum of un-piled-up pulses, which constitute the measurement's independent data. The best that we can do, therefore, is to scale these counts into the corrected spectrum without losing any additional information. We show several different methods by which optimal averages <C> can be formed in practice. Even better accuracy may be obtained at high input count rates (ICRs), where the possibility of pileup in the fast filter becomes significant, by generating estimates of counts lost to fast channel pileup, and adding such estimates to <C>.

The present invention does not require a livetime measurement or clock of any kind, which therefore distinguishes it from the methods of Westphal and Bingham. Two innovations distinguish the method from that of Harms: first, the requirement that a correctly formed average number of input counts <C> be added to the MCA each time a good count is found, rather than just the actual number of input counts preceding a good count; and, second, that when <C> is properly formed, the standard deviations in the uncorrected MCA spectrum can be scaled to compute accurate values of the standard deviations in the corrected MCA spectrum via Eqn. 3, using the same scaling equations (Eqns. 2) previously used in static ICR measurements with non-extending livetime measurements.

Our several methods for estimating <C> differ in the details of how we form the average and what resources are required to implement it. A conceptually simple approach, based on the definition of <C>, would be to count, for a sequence of M non-piled-up pulses, the number $N_i$ of pulses detected in the fast channel for each member i of the sequence; and form <C> as the average of the M values of $N_i$.

In a preferred first "running" averaging method we implement this in a computationally efficient way by counting the number $N_i$ of input counts arriving before each good count, including the good count, and include it in a running sum of M input count measurements wherein we compute the newest estimate $<C>_i$ from the preceding estimate $<C>_{i-1}$ by the equation $<C>_i=<C>_{i-1}+(N_i-N_{i-M})/M$. Requiring M to be a power of 2 (i.e., $M=2^L$) allows us to perform the required division merely by shifting $(N_i-N_{i-M})$ by L bits. In this method <C> is not an integer and the L bits of precision must be retained in the corrected MCA spectrum. A single count is also added to the same bin of the uncorrected MCA spectrum. The accuracy with which standard deviations in the corrected spectrum can be estimated from the uncorrected spectrum depends upon the value of L. Values of L equal to 4 or more are generally adequate, with L equal to 5 giving a quite precise result. Larger values of L take longer to adjust to changes in input count rate and therefore are less satisfactory when the best time domain performance is desired. For example, at 200 kcps ICR and 90% dead time, the L=4 average takes 0.8 ms to fully adjust to a change in ICR, the L=5 average takes 1.6 ms, both of which are very fast. The same method can be used with M not equal an integer power of 2, but the divisions are not so simply implemented.

In a second "bucket" averaging method, which only requires storing integer MCA values, a counter is incremented by 1 every time an input count is detected and decremented by <C> each time a good count is detected and the value <C> is stored in the corrected MCA spectrum at the location given by the energy of the good count. A single count is also placed into the uncorrected spectrum as in the previous cases. Every M good counts, the residual value in the counter is divided by M and <C> is adjusted by the quotient, rounded to the nearest integer value, which may be negative. All input counts are thereby distributed into the corrected spectrum. The same comments regarding the value of M, and whether or not it can be expressed as an integer power of 2, apply as in the first averaging method.

In a third "circular" averaging method, which also only stores integer MCA values, a circular memory of length M is addressed by two pointers, a fast pulse pointer $P_F$ and a good pulse pointer $P_G$. Each time an input count is detected, the memory value at $P_F$ is incremented by one and $P_F$ is incremented by one, modulo M. Each time a good output count is detected, the memory value at $P_G$ is added to the corrected MCA spectrum in the bin given by the energy of the good count, the memory value at $P_G$ is zeroed, and $P_G$ is incremented by one, modulo M. And, again, a single count is also added into the same bin of the uncorrected MCA spectrum.

Through the use of Monte Carlo modeling methods we compared the performance of these methods to each other and to the Harms method. All methods were found to produce unbiased corrected MCA spectra. The standard deviations in these corrected spectra, however, differed markedly between the methods. The Harms method was worst, producing standard deviations that were 40% larger than those from Eqns. 2a–2c at large deadtimes. For M equal to 32, the circular averaging method's standard deviations exceeded Eqns. 2a–2c by a maximum of 10%, with an average of 5%, a significant improvement over Harms' method. For M equal to 16 and 32 (L equal to 4 and 5), the bucket averaging method's standard deviations exceeded Eqns. 2a–2c by 4.0% and 2.6% respectively, with nearly flat distributions as a function of ICR. The running average method produced the best performance. For M equal to 16 and 32, its standard deviations exceeded Eqn. 2 by only 1.7% and 0.4% respectively, with very flat distributions as a function of ICR. These methods, therefore, are capable of simultaneously producing accurate spectra in the presence of rapidly varying ICRs and achieving the same minimal standard deviations in these spectra as can be attained in the case of static ICRs. In particular, the accuracies of their standard deviation estimates improve over the method of Harms by between one and two orders of magnitude.

All of these methods only distribute counts detected in the fast channel into the corrected MCA spectrum. They are therefore incapable of properly correcting the MCA spectrum for counts lost to pileup in the fast channel. We have therefore devised an enhancement to our methods which accurately corrects for these losses. In this enhancement, we measure the output count rate $OCR_{fm}$ of detected pulses in the fast channel filter pileup inspection circuit and use it, from time to time, to estimate the probability P that any individual detected pulse suffers from pileup in the fast channel. We then use P to correct our estimates of <C> for counts lost to pileup in the fast channel. To aid in this process we have developed a universal curve relating P to the measurable quantity $\tau_{df} \times OCR_{fm}$, where $\tau_{df}$ is the fast channel dead time and $OCR_{fm}$ is the measured fast channel output count rate. By generating a table of values of P versus $\tau_{df} \times OCR_{fm}$, the process of generating P for a measured $OCR_{fm}$ can be reduced to a table lookup, possibly with interpolation.

When we are dealing with non-integer values of <C>, as in the running average method, the correction to <C> is made by simply replacing the addition of 1 by the addition of 1+P to the fast pulse counter each time an additional fast pulse is detected, and otherwise carry out the method as before. If we wish to restrict our method to integer arithmetic, as we will for the circular average method and may wish to for the bucket average method, we cannot simply add in the non-integer value of P. Instead, each time a fast pulse is detected we generate a random number, using a generator that produces uniform probabilities between 0 and 1, and compare it to P. If the random number is smaller than P, a second count is added to the fast channel averaging procedure. Either procedure results in a method that precisely adjusts the corrected MCA spectrum for all counts lost to fast pileup and, further, can do so with standard deviations that are less than 1% larger than the minimum value represented by Eqn. 2. Since, for a specific value of $\tau_{df}$, the values of P depend solely upon the value of $OCR_{fm}$, they can be pre-computed and stored in a small lookup table where they can be accessed without the need for further computation. The enhanced method is therefore capable of producing spectra that are statistically accurate even at very high count rates which fluctuate on the millisecond time scale.

While our preferred implementations are digital, with the exception of the formation of the proper input count averages, digital processing techniques are not generally required by the invention, which could equally well be implemented using classical analog spectroscopy techniques in the various filtering and inspection steps. We discuss this approach briefly. Further, while we present our invention primarily in the context of radiation spectroscopy using solid state detectors, the underlying methods apply equally well to other spectroscopies, including nuclear and particle spectroscopies, which use the same fundamental filtering and pulse counting techniques.

A further understanding of the nature and advantages of the present invention may be realized by reference to the remaining portions of the specification and the drawings.

BRIEF DESCRIPTION OF THE DRAWINGS

FIG. 7 shows Monte Carlo modeling results for the OCR/ICR ratio and scaled deviation ratio when lost count averaging is implemented using 32-point circular averaging;

FIG. 9 shows Monte Carlo modeling results for the scaled deviation ratio when the invention's lost count averaging is implemented using 16- and 32-point bucket averaging;

FIG. 14A shows Monte Carlo modeling results, using 32-point running averaging, for both corrected output counts and the scaled deviation ratio when fast pileups are included in the model but are not corrected for.

DESCRIPTION OF SPECIFIC EMBODIMENTS

1. Introduction

Figure 1:
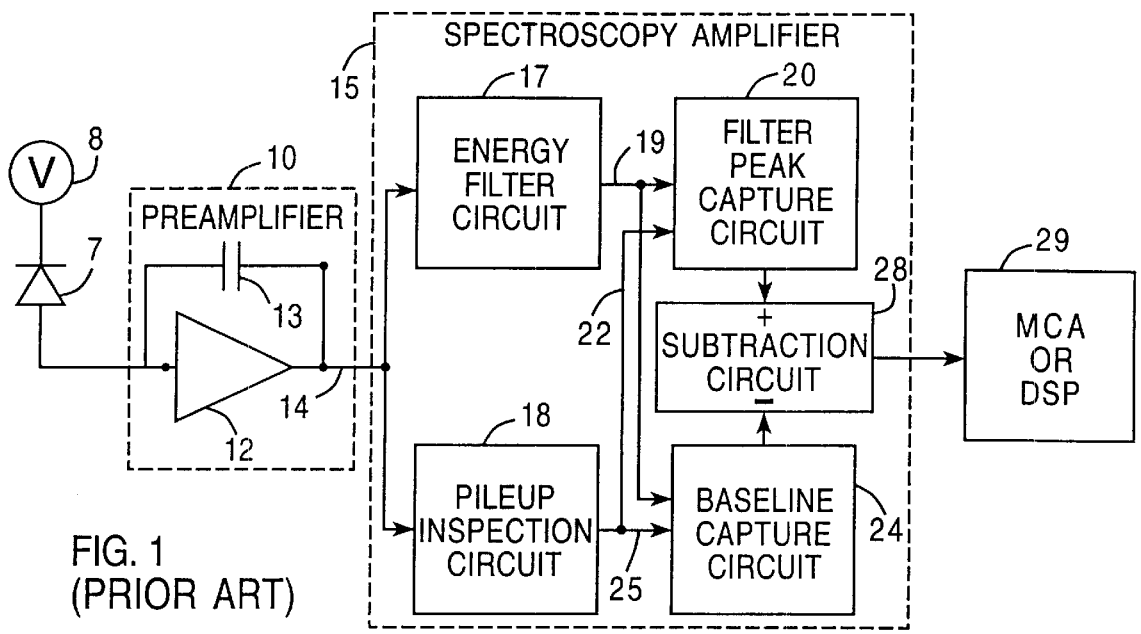
FIG. 1 is a block diagram of the major function components in a prior art radiation spectrometer.

In order to explain the invention method, we begin with an analysis of the prior art method of Harms [HARMS 1967]. As noted earlier, this method generates a corrected MCA spectrum by adding to it, each time a good event is detected, one plus the number of prior pile-up events since the last good event. The method is known to produce correct spectral results at fairly high input counting rates (ICRs) but the statistics of those results are unknown. [JENKINS 1981] We therefore developed a Monte Carlo model to investigate. The first step was to develop a generator which produced a sequence of events whose intervals were randomly distributed according to Poisson statistics for a selected ICR. For a selected peaking time, the interval between each event and its predecessor was compared to an appropriate inspection period and both events were classified as piled-up or not as that interval was found to be less than or greater than the inspection period. To survive this process as a good event, an event therefore had to be separated from both its predecessor and successor by times exceeding the inspection period. The number N of piled-up events occurring between each good event and its preceding good event was counted for inclusion in an MCA spectrum. In order to collect statistics on the MCA spectrum, a flat distribution of 100 spectral channels was used. Two spectra were generated, an uncorrected ("classical") spectrum and a corrected spectrum. Therefore, each time a good event was found, a random number between 0 and 99 was generated, 1 was added to the classical spectrum in that bin and N+1 added to the corrected spectrum in that bin. A total of 10 million counts was generated, so that the expectation number of counts in each corrected MCA bin was 100,000. The averages and standard deviations from the averages were then computed for both spectra, the average from the classical spectrum being the average output counting rate (OCR), the average from the corrected spectrum the ICR.

Two tests showed that the model was working correctly. First, within statistics, the standard deviation of the classical spectrum from its mean was always (within statistics) equal to the square root of the average number of counts, as is expected classically for Poisson statistics. Secondly, the mean of the corrected spectrum, provided that there was assumed to be no pileup in the fast channel, was always 100,000, so that no counts were lost. Therefore, to compare the statistical distribution of the counts in the corrected MCA spectrum to the classical spectrum, we developed the "scaled deviation ratio" R, based on Eqns. 2a–2c:

$$R=(\sigma_c <N>_u)/(\sigma_u <N>_c), \quad (4)$$

where $<N>_u$ and $<N>_c$ are the mean values in the uncorrected and corrected spectra, and $\sigma_u$ and $\sigma_c$ are their standard deviations. Thus, R will be equal to unity when the corrected spectrum has the same statistics as in the case of correcting for pileup when the ICR is static. If the correction process introduces additional variation, R will exceed unity.

Figure 4:
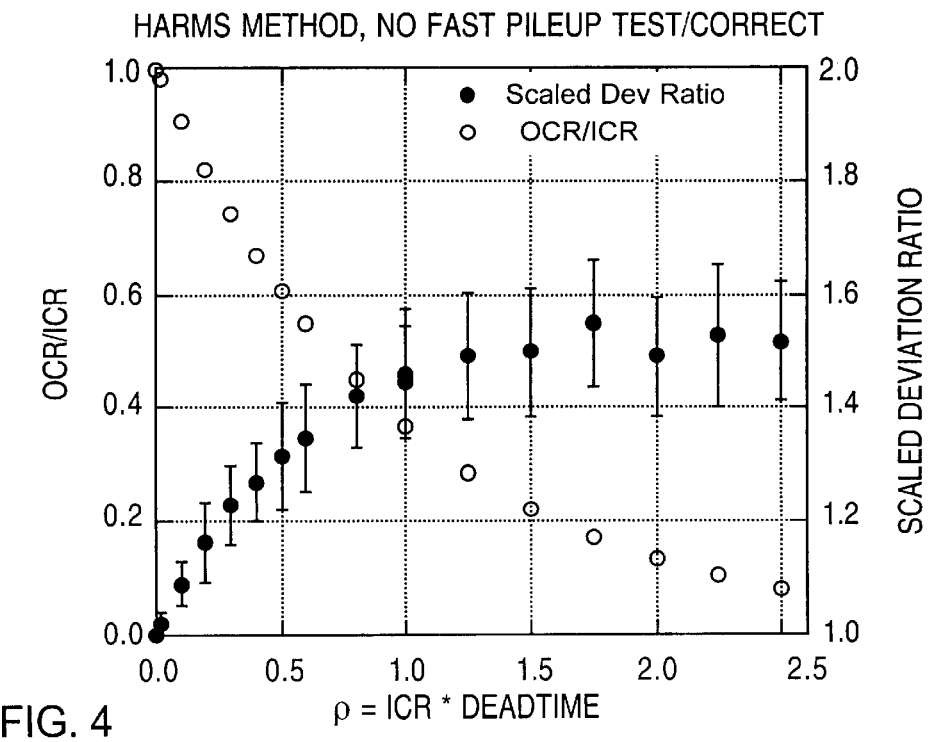
FIG. 4 shows Monte Carlo modeling results for the OCR/ICR ratio and scaled deviation ratio from the prior art Harms pileup correction method.

FIG. 4 shows the Monte Carlo modeling results for OCR/ICR and R for the Harms pileup correction method plotted versus $\rho$, the Poisson distribution parameter equal to ICR*$\tau_{sd}$, where $\tau_{sd}$ is the dead time in the slow energy filter channel and is equal to twice the pileup inspection period. Since the Poisson distribution depends only upon $\rho$ and not upon ICR or $\tau_{sd}$ individually, these results will be generally true for all peaking times. The model calculations were carried out for $\rho$ values between 0 and 2.5, which is approximately equivalent to a 90% deadtime. The point of maximum throughput occurs at $\rho$ equal to 1, where OCR equals ICR/e. As expected, OCR/ICR drops smoothly and exponentially from 1 at $\rho$ equal to zero to 0.085 at $\rho$ equals 2.5. Also as expected, OCR/ICR results were found to be independent of which averaging method we employed and will not be discussed further or shown in the following figures.

Our Monte Carlo results therefore show that, as Jenkins et al. [JENKINS 1981] had suggested it might, the Harms' method adds additional uncertainty into the corrected spectrum results, compared to what can be achieved by simply scaling results by the ICR/OCR ratio in a static ICR situation. R is seen in FIG. 4 to start at unity for $\rho$ equal to zero (i.e., at zero ICR) and rise to saturate at the value of about 1.5 for $\rho$ values greater than 1.25. In FIG. 4, as in all the modeling results that we present, the error bars on the R points are the standard deviations found between the mean value of $\rho$ and the values in the individual channels in our 100 channel corrected MCA spectrum. Our brief conclusion, then, is that for values of $\rho$ much above 1.25, the Harms' method introduces about 50% more uncertainty into the corrected MCA spectrum than would be generated by static methods.

2. Averaging Methods Without Fast Pileup Correction

The averaging methods presented in this section all assume that no fast pulse pileup occurs, which is equivalent to assuming that fast channel dead time is zero. While this case can never be truly achieved in practice, it serves two purposes: first, to establish theoretical limits and, second, to provide a reasonably accurate description of cases where the energy filter deadtime is much longer than the fast channel deadtime. This situation is commonly achieved in x-ray work, where the ratio of the two dead times may approach or exceed 100. In Sec. 3 we will show how to accurately correct for fast pileup losses as well.

Figure 2:
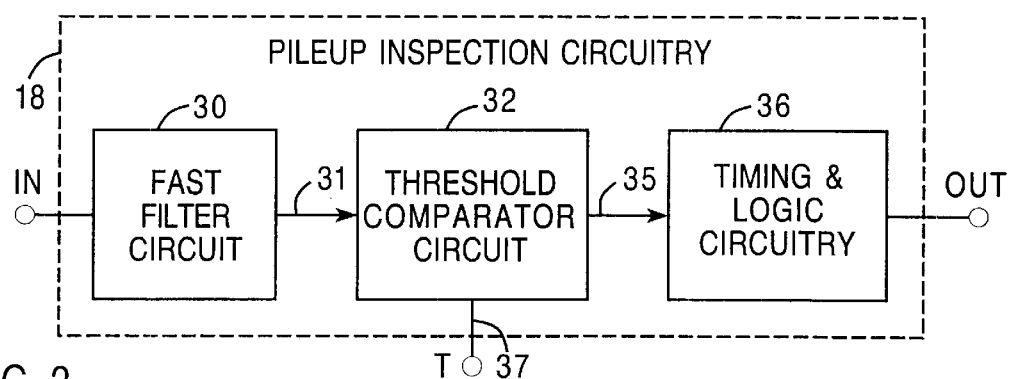
FIG. 2 is a block diagram of the pileup inspection circuitry in the prior art spectrometer in FIG. 1.
Figure 5:
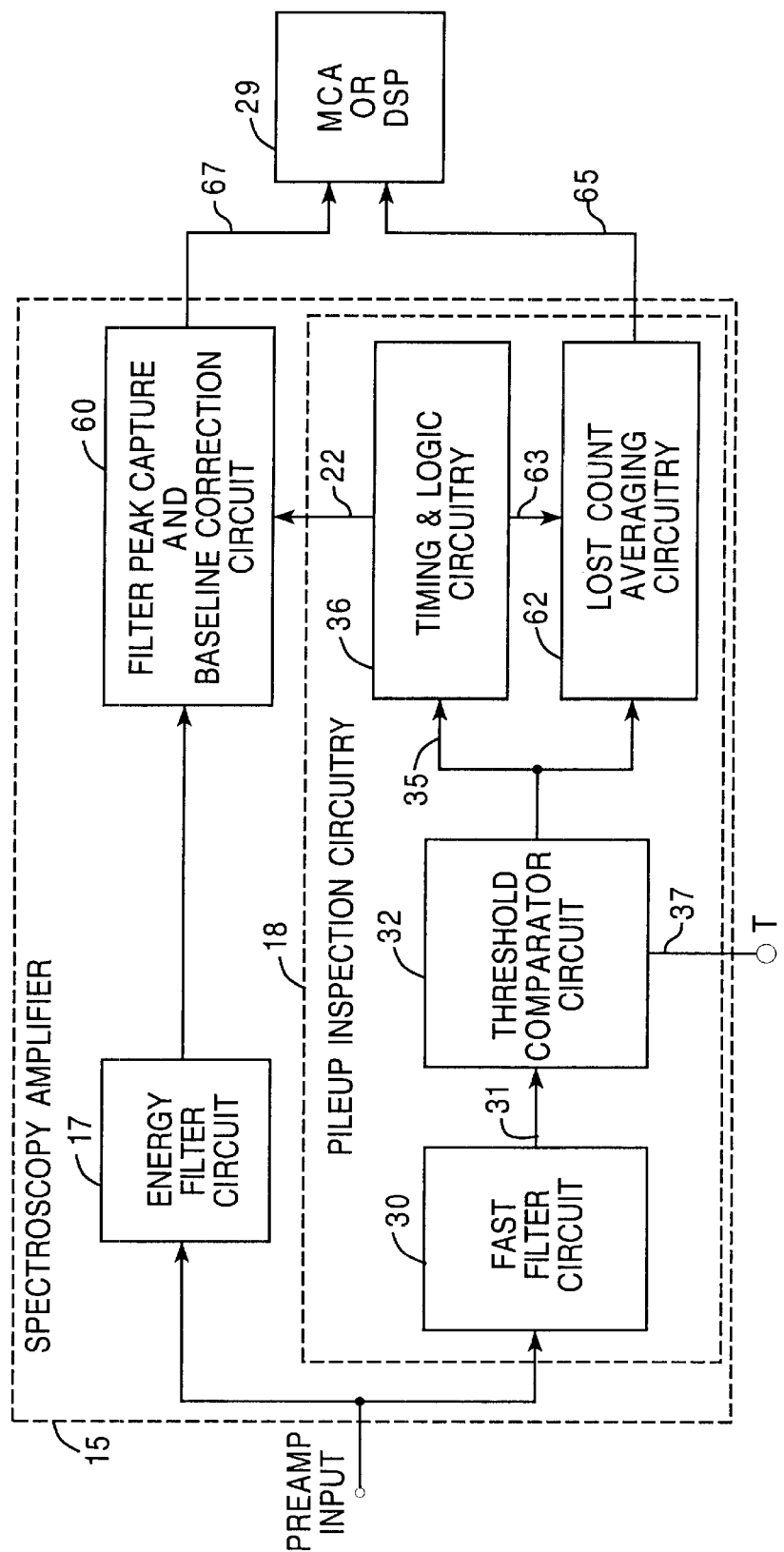
FIG. 5 is a block diagram of circuitry for implementing the invention.

In a preferred implementation, exclusive of the particular averaging method employed, we modify the prior art designs of FIG. 1 and FIG. 2 as shown in FIG. 5. Purely for convenience of representation, the functional blocks 20, 24, and 28 have been collapsed into the single functional block 60 which implements the same filter peak capture 20, baseline capture 24 and subtraction 28 functions as before and, when a good peak value is captured, passes its baseline corrected value to the MCA or DSP 29. Our earlier comments that it is functionally immaterial whether the baseline correction circuitry is actually located within the spectroscopy amplifier 15 or DSP 29 also apply to the present design. The inventive addition to spectroscopy amplifier 15 lies in the addition of the lost count averaging circuitry 62 added to pileup inspection circuitry 18 and the functions included therein, which shall be described below. In particular, we have described the rest of the spectroscopy amplifier 15 in functional terms and without reference to whether it is implemented using digital, analog, or mixed digital-analog circuitry since the inventive methods can be applied equally well in all these cases.

The overall operation of the modified circuit differs as follows from the prior art circuits described above. First, each time the timing and logic circuit 36 detects a good count and signals the filter peak capture circuit 60 to capture its peak value, it also strobes the lost count averaging circuit 62 via line 63. Second, the lost count averaging circuit is also connected to the threshold comparator circuit 32 via line 35 and so receives a pulse for each detected count, whether it is piled up on not, just as the timing and logic circuitry 36 does. Third, by means to be described below, the lost count averaging circuit dynamically forms estimates of the average number <C> of input counts that occur for each detected good count and updates these estimates continually as the data collection proceeds. Fourth, each time a good count is detected, the lost count averaging circuit 62 sends its current estimate of <C> on line 65 to the MCA or DSP 29 to be used in binning the peak amplitude captured by the filter peak capture circuit 60 and passed on line 67 to the MCA or DSP 29. Fifth, for each good pulse, the MCA or DSP 29 makes additions to two spectra: first, in a classical uncorrected spectrum, it adds the value 1 to the bin associated with the captured peak value; second, in a corrected spectrum, it adds the estimate of <C> to the equivalent bin. Finally, when data collection is complete, the standard deviation $\sigma_{ci}$ of the counts $N_{ci}$ the $i^{th}$ bin in the corrected spectrum is computed for all values of i using both $N_{ci}$ and the counts $N_{ui}$ in the same $i^{th}$ bin in the uncorrected spectrum according to Eqn. 3. Thus, as noted above, though our data acquisition method is novel, we employ the same method for estimating standard deviations in our corrected spectrum as is presently used to estimate the standard deviations in corrected spectra collected by non-livetime-extending spectrometers operating under constant ICR conditions.

In the following, we describe three methods for implementing the lost count averaging circuitry 62, proceeding from the least accurate (circular averaging) to the most accurate (running averaging). Our descriptions will be in the form of logical flow charts since the actual circuitry can be equally well implemented using a wide variety of means, including hardwired logic, gate arrays, and microprocessors or DSPs, and, given the flow charts, these implementations are readily carried out by those skilled in the art of these various means.

Circular Averaging Method

Figure 6A:
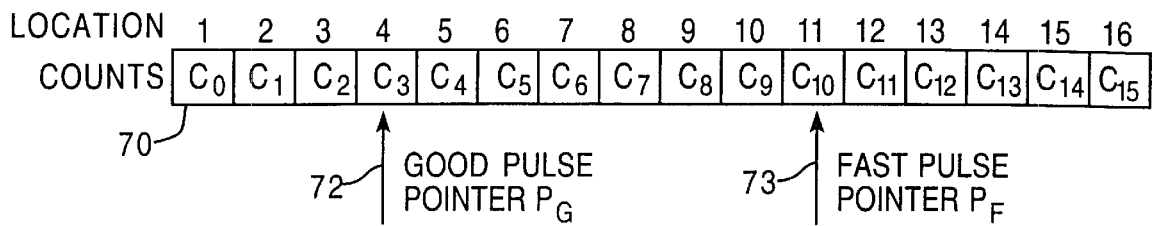
FIG. 6A is a diagram showing a memory structure for implementing the invention's lost count averaging circuitry using circular averaging.
Figure 6B:
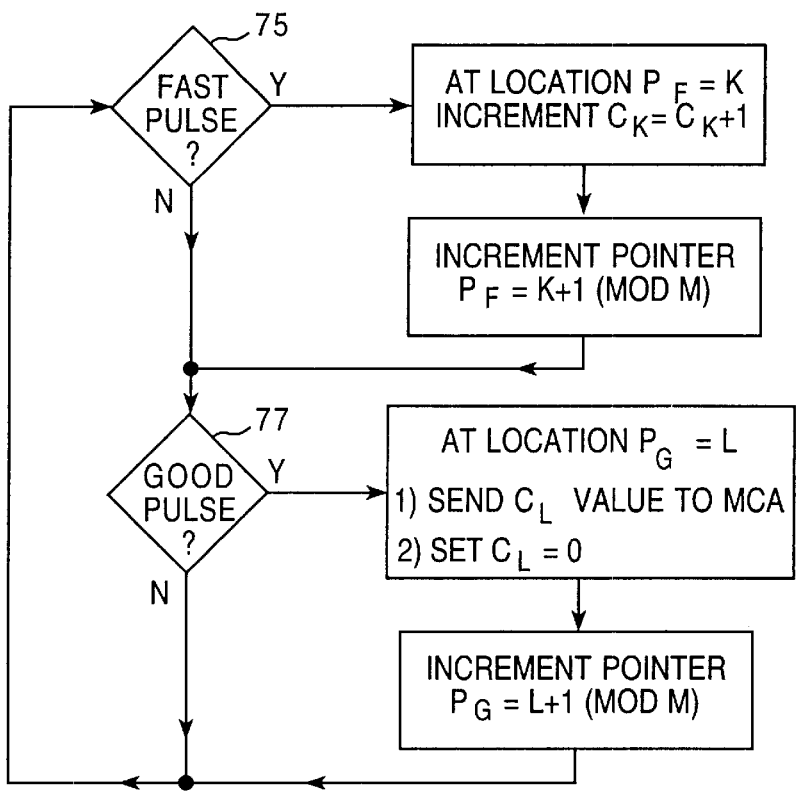
FIG. 6B is a flow chart of circuitry for implementing the invention's lost count averaging circuitry using circular averaging.

The circular averaging method uses a circular buffer memory 70, as shown in FIG. 6A and FIG. 6B, addressable by two pointers: a good pulse pointer $P_G$ 72 and a fast pulse pointer $P_F$ 73. For a given buffer length M, the pointer arithmetic is computed modulo M, so that, for example, when $P_F$ equals M−1 and is incremented by 1, it wraps around to become equal to 0 again. In this method, the lost count averaging circuit 62 operates as shown in FIG. 6B. When it receives a signal via line 35 that a fast pulse has been detected, it follows the "yes" branch from test 75, adding 1 to the value $C_K$ stored at location K pointed to by the fast pulse pointer $P_F$ and then increments $P_F$ by 1 modulo M. When the circuit receives a signal via line 63 that a good pulse has been detected, it follows the "yes" branch from test 77 and, at the location L pointed to by the good pulse pointer $P_G$, sends the stored value $C_L$ on line 65 to the MCA or DSP 29; sets $C_L$ to zero; and then increments $P_G$ by 1 modulo M. By this means, the numbers $C_L$ sent to the MCA are samples of the average value of fast counts detected per slow count received.

FIG. 7 shows results obtained from Monte Carlo modeling this method when M equals 32. The scaled deviation starts at unity, similarly to the Harms method, but only rises to a peak value of about 1.1 for values of $\rho$ near to 0.5 and then drops back to 1.02 for $\rho$ near to 2.5. Our understanding of this behavior is that it has the same source as the Harms deviations: namely that statistical fluctuations in the estimates $C_L$ added to the number $N_{ci}$ in a particular spectral bin i result in increased variation in its resultant value. Such fluctuations are larger in the Harms method, however, where they are not averaged at all. Therefore, in order to reduce the scaled deviation ratio, our averaging method should minimize statistical fluctuations in its <C> estimates.

Bucket Averaging Method

This method works to minimize fluctuations in the estimated average fast pulse arrival rate C by averaging fast count arrival rates over sets of M good counts and only updating the estimate <C> of C at those intervals. A logic diagram for the bucket averaging method is shown in FIG.

8. When a fast pulse is detected, the "yes" branch of test 79 causes a fast pulse counter F to be incremented by 1. When a good pulse is detected, the "yes" branch of test 80 causes three actions to occur: first, the value <C> is sent to the MCA or DSP 29; second, the fast pulse counter F is decremented by the amount <C>; and, third, a good pulse counter G is incremented by 1. F, therefore, accumulates any residual differences between $<C>_T$, the true average value of <C>, and the current estimate being sent to the MCA. When the value of the counter G reaches the preset value M, the "yes" branch of test 81 causes the quotient of F/M, rounded to the nearest integer, to be added to <C> and also resets the good pulse counter G to zero. In order to assure that all fast pulses are eventually distributed into the corrected spectrum, the fast pulse counter F is never reset to zero. A particular feature of this method is that it only deals with integer values of C, which may be easier to implement in certain technologies and also does not require the storage of non-integer values in the corrected spectrum. The rounded values of F/M, of course will have both positive and negative values as required to approximate $<C>_T$ and, particularly, to track $<C>_T$ when it is decreasing in time. While, in general, M can be any integer, it is particularly convenient when $M=2^L$ is an integer power of 2, in which case the division F/M is trivially carried out by a bit shifting operation which is readily implemented in a programmable gate array.

Figure 8:
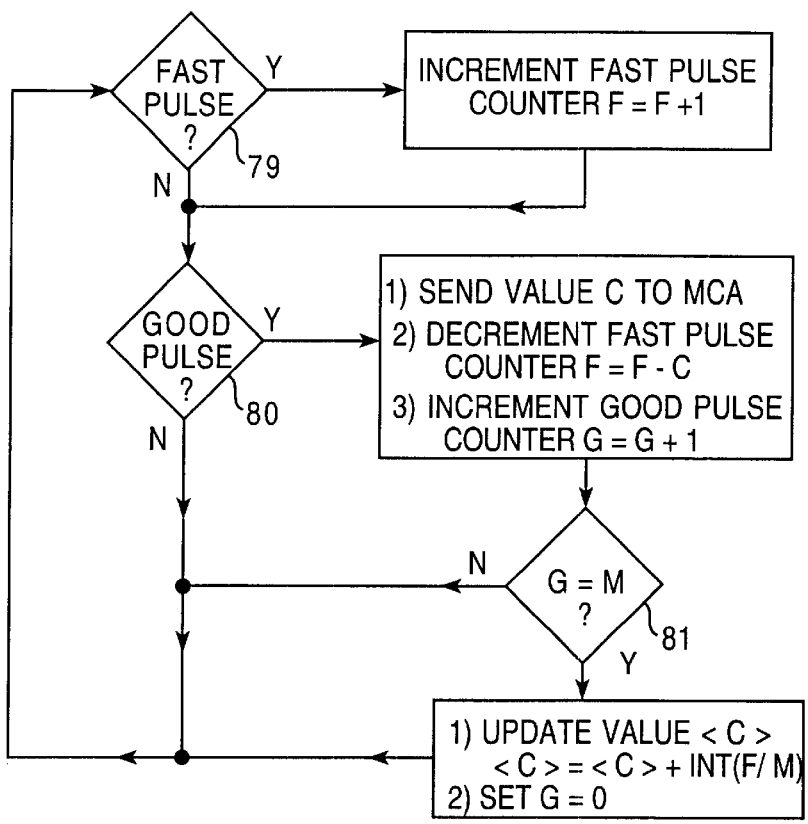
FIG. 8 is a flow chart of circuitry for implementing the invention's lost count averaging using bucket averaging.

FIG. 9 shows results obtained from Monte Carlo modeling this method for values of M equal to 16 and 32. The scaled deviation ratio is always slightly greater than unity, but not by much, and has very little dependence on the value of the normalized incoming count rate ρ. The average value of the scaled deviation ratio for p from 0 to 2.5 is 1.040±0.012. Increasing M to 32 improves performance significantly. There is now a bit of a peak in the scaled deviation ratio, to about 1.035, at ρ equal to 0.3, but for the most part the values lie quite close to unity. Its average value for ρ from 0 to 2.5 is 1.026±0.017. Clearly unity could be even more closely approached by increasing M. However, the larger the value of M is, the longer it takes the method to respond to changes in incoming count rate. Selecting an M value therefore represents making an engineering tradeoff between a desire for accuracy in calculating standard deviations for the corrected spectrum and a desire for rapid response time in the face of changing incoming count rates. Different values of M will be appropriate in different circumstances. However, as a brief inspection of FIG. 8 will reveal, it is straightforward to construct an implementation wherein M is an adjustable parameter and readily changed to accommodate the measurement situation.

Running Averaging Method

Figure 10:
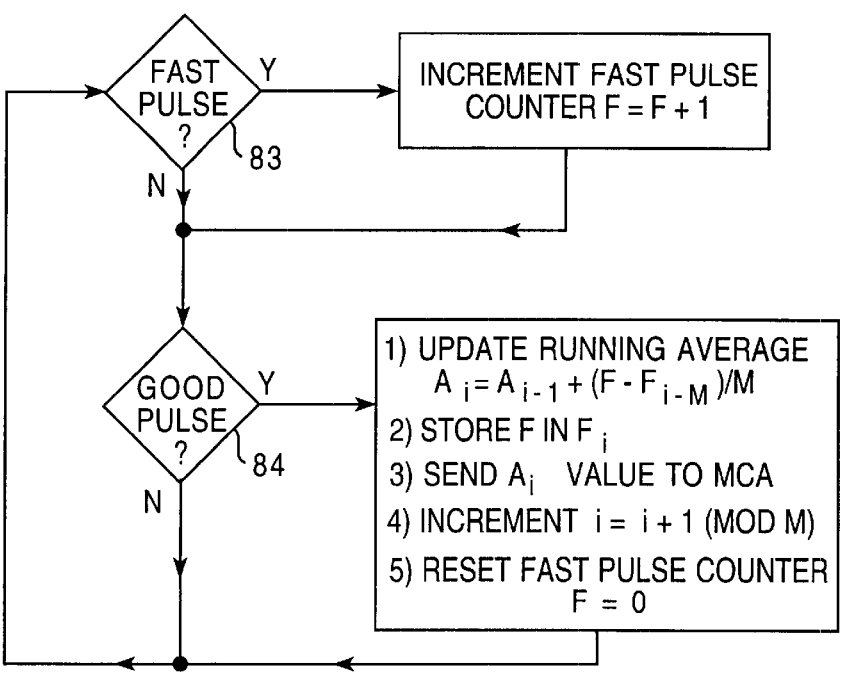
FIG. 10 is a flow chart of a circuit implementing the invention's lost count averaging using a running average method.

This method works to minimize fluctuations in the estimated average fast pulse arrival rate C by averaging fast count arrival rates over the last M good counts and updates the estimate of C each time a good pulse is detected. In principle, this can be implemented by summing the values $F_i$ of fast pulse counts over the last M events i and dividing by M. However the same result is obtained more rapidly, and with fewer resources, using a running average instead. A logic diagram for the running average method is shown in FIG. 10. Not shown is an addressable memory of length M which is used to store recent values of fast pulse counts. When a fast pulse is detected, the "yes" branch of test 83 causes a fast pulse counter F to be incremented by 1. When a good pulse is detected, the "yes" branch of test 84 causes five actions occur. First, the value F is stored in memory location i as $F_i$. Second, an updated estimate of <C> is computed according to the programming language equation:

$$<C>=<C>+(F-F_{i-M})/M. \tag{5}$$

Third, the value <C> is sent to the MCA or DSP 29. Fourth, i is incremented by 1, modulo M. Finally, fifth, the fast pulse counter F is reset to 0. As per the discussion of the bucket averaging method, in a preferred implementation M will be an integer power of 2, typically 16 or 32, because it allows Eqn. 5 to be readily implemented in a programmable gate array. If it method is implemented explicitly as shown in Eqn. 5, the computed values of <C> are not integers and the physical embodiments of FIG. 10 should be designed to accommodate this characteristic of the method. Alternatively, the division by M may be eliminated at this step and carried out later on the collected spectrum once data collection is complete. In either case, M additional bits of data should be preserved throughout to avoid truncating <C>.

Figure 11:
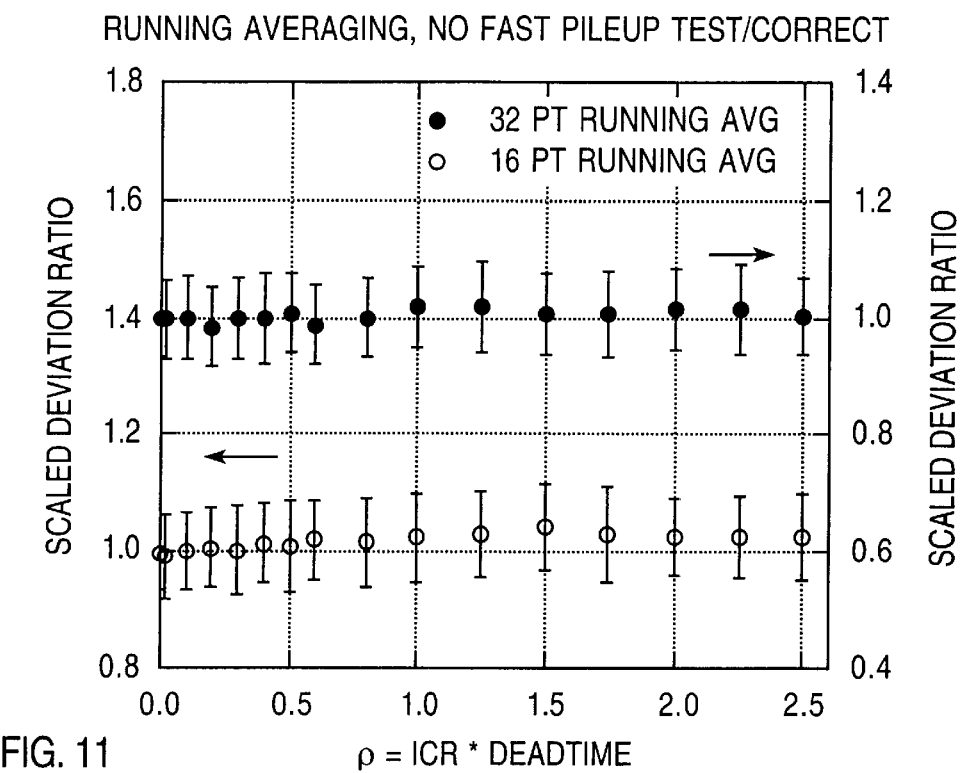
FIG. 11 shows Monte Carlo modeling results for the scaled deviation ratio when the invention's lost count averaging is implemented using 16- and 32-point running averaging.

FIG. 11 shows results obtained from Monte Carlo modeling this method for values of M equal to 16 and 32. The accuracy of the method is superior to the previous two, particularly for lower count rate values. For M equal to 16, the maximum scaled deviation ratio is only 1.04 and its average for ρ between 0 and 2.5 is 1.017±0.014, which is better than the bucket method for M equal to 32. For M equal to 32, the running average method gives a scaled deviation ratio that is always equal to unity, within statistical fluctuations. Its average for ρ between 0 and 2.5 is 1.004±0.010. Thus, for this method, Eqn. 3 becomes exact for estimating standard deviations in the corrected spectrum.

The time response of this method should be adequate for most situations. For a first example, suppose that, for an ICR value of 100,000 cps, ρ equals 1.0, the point of maximum throughput. The OCR will then be 100,000/e=36,800 cps and the characteristic response time will be either 16/36,800=0.44 ms, for M equal to 16, or twice that, 0.87 ms, for M equal to 32. For a second example, suppose that for an ICR value of 200,000 cps, ρ equals 2.3, the point of 90% deadtime. Here the OCR will be 20,000 cps and the response times for M=16 and 32 will be 0.8 ms and 1.6 ms, respectively. Thus the method is capable of tracking changes in the input counting rate on the millisecond time scale even at quite high deadtimes.

3. Adding Fast Pileup Correction to the Averaging Methods

The Fast Pileup Issue

Figure 3:
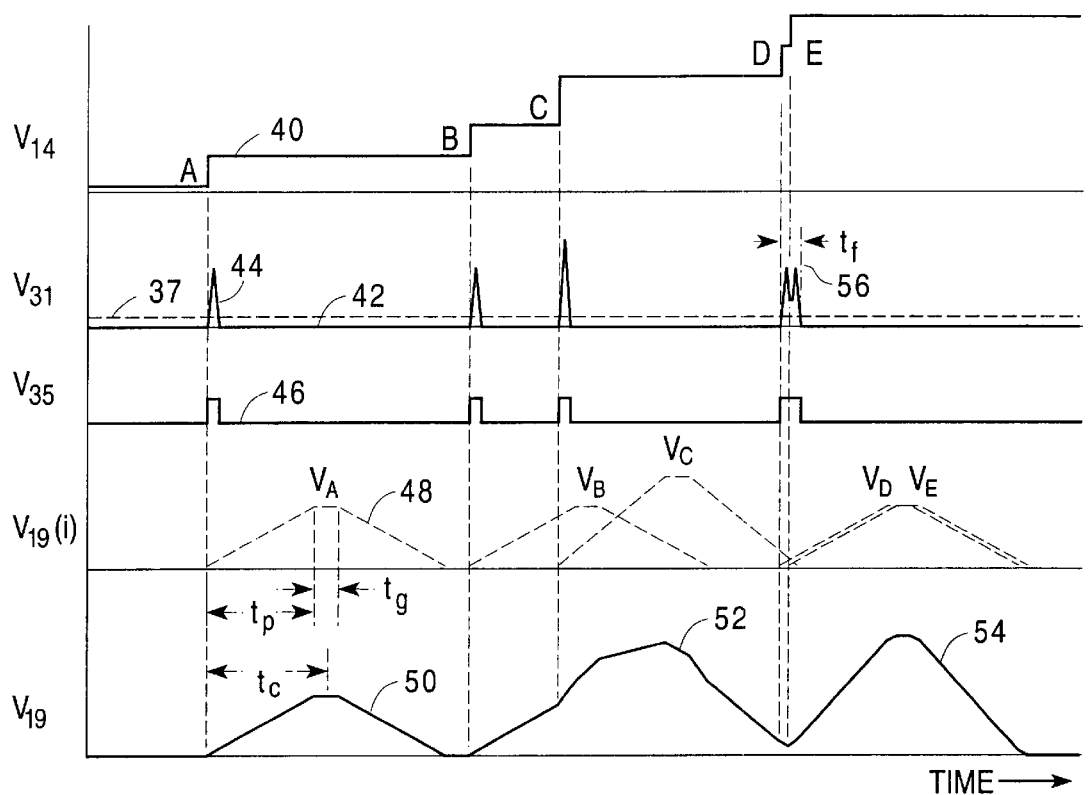
FIG. 3 shows the outputs of the preamplifier and filter circuits in FIG. 1 in response to various sequences of signal events.

The heart of the fast pileup issue is shown in FIG. 3, trace $V_{31}$, where we see that, in the case of fast pileup, two consecutive pulses arrive so closely in time that the output of the fast filter 56 does not drop below the threshold value T 37 between them. Thus only a single event is "seen" by the timing and logic circuitry 36 and only a single count added to any of our estimates of <C>. The extra fast pulses are lost.

Correcting for Lost Fast Pulses

Because Eqn. 1 also applies to the fast filter, we can use it to create an estimate of the probability that any detected fast pulse is actually a piled-up pulse, so that 2 should have been added to our procedure for estimating <C> rather than 1. Thus, using the subscripts f for "fast" and t and m for "true" and "measured" respectively, we can write:

$$P=(ICR_{ft}-OCR_{fm})/OCR_{fm}=\exp(\Delta)-1, \tag{6a}$$

and $$\tau_{df} \times OCR_{fm} = \Delta\exp(-\Delta), \tag{6b}$$

where $$\Delta \times \tau_{df} \times ICR_{ft}. \tag{6c}$$

Here $\tau_{df}$ is the deadtime in the fast channel, $OCR_{fm}$ is the measured output count rate from the fast channel, $ICR_{ft}$ is the immeasurable true fast channel input count rate, and $\Delta$ is a parameter that depends on both $\tau_{df}$ and $ICR_{ft}$. $\tau_{df}$ will be characteristic of the fast channel circuit and can be measured by various techniques that are well known to those skilled in the art.

Figure 12:
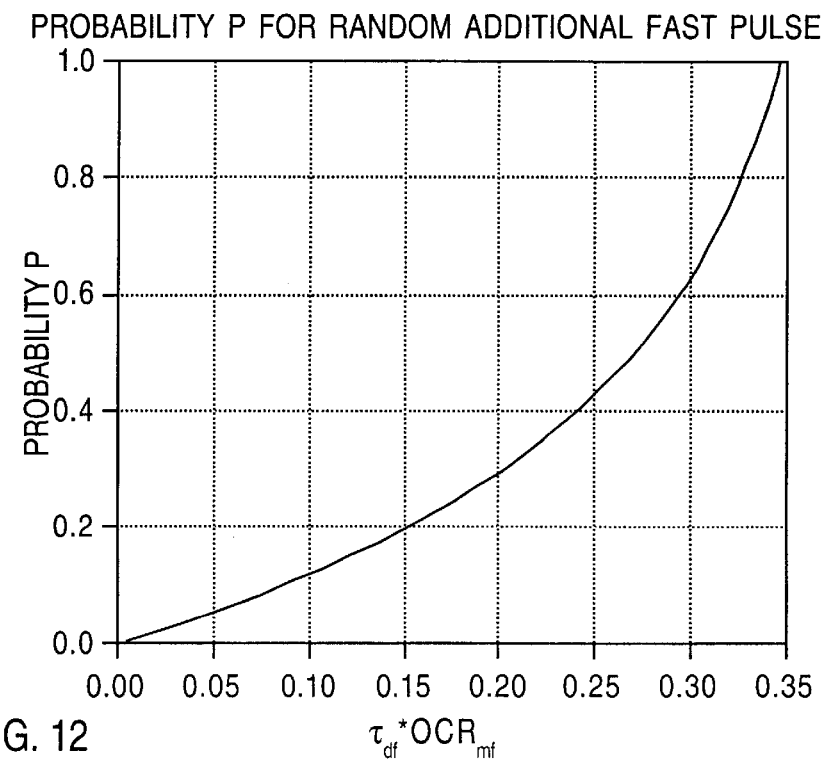
FIG. 12 shows a universal curve relating the probability of fast pileup to the normalized measured fast output counting rate.

Therefore, if we make a plot of P versus $\tau_{df} \times OCR_{fm}$, we will obtain a universal curve, FIG. 12, parameterized by values of $\Delta$. The value of FIG. 12 is that, although we cannot measure either $\Delta$ or $ICR_{ft}$, we can measure both $\tau_{df}$ and $OCR_{mf}$ and, therefore, use the plot to determine what the probability P of fast pileup is for any particular value of $OCR_{mf}$ at which our spectrometer happens to be operating. In particular, if we count $N_{fm}$ fast pulses in time $\Delta t$, we can compute the x coordinate value in FIG. 12 according to $x=\tau_{df} \times N_{fm}/\Delta t$ and then read off P from the figure. Further, if carrying out divisions is too time consuming, then, since both $\tau_{df}$ and $\Delta t$ are constants for a particular set of spectrometer parameters, we can simply calculate a set of values of P versus $N_{fm}$ for that value of $\tau_{df}/\Delta t$ and store them in a lookup table for rapid access.

A Preferred Running Average Implementation Including Fast Pileup Correction

Figure 13:
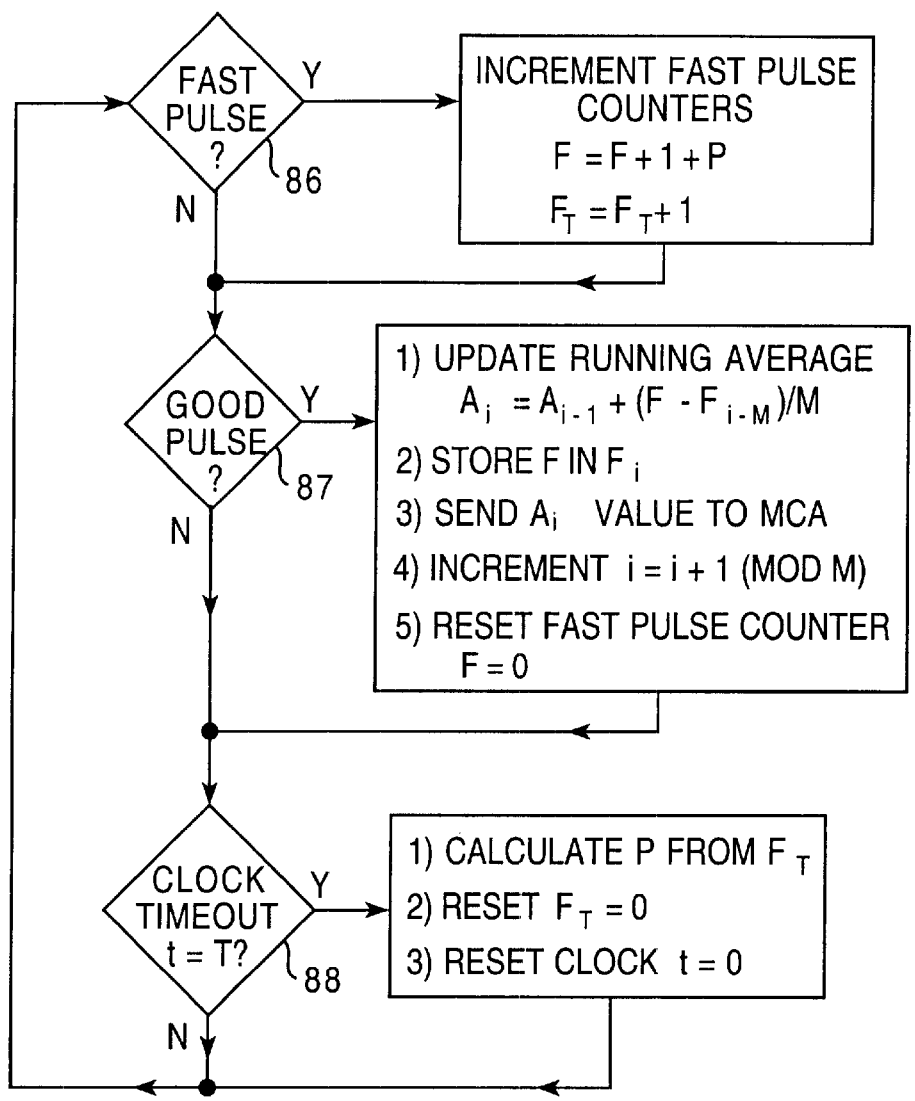
FIG. 13 shows the flow chart of FIG. 10 augmented to also correct for fast pileups.

Using the universal correction curve FIG. 12, we can then implement the lost count averaging circuitry 62 of FIG. 5 according to the logic diagram of FIG. 13. This method repeats the running average method from FIG. 10 for computing <C>, but uses an estimate P of the true fast counts to increment the fast pulse counter.

When a fast pulse is detected, the "yes" branch of logic test 86 causes two fast pulse counters to be incremented. A total detected fast pulses counter $F_T$ is incremented by 1. The estimated fast pulse counter, F is incremented by 1+P, where P is the current estimate of the probability that the fast pulse was piled up.

When a good pulse is detected, the "yes" branch of test 87 causes exactly the same five actions to occur as in the running average method described above. First, the value F is stored in memory location i as $F_i$. Second, an updated estimate of <C> is computed according to Eqn. 5. Third, the value <C> is sent to the MCA or DSP 29. Fourth, i is incremented by 1, modulo M. Finally, fifth, the fast pulse counter F is reset to 0.

The distinctive step of this method occurs when a preset clock times out at time T. Then the "yes" branch of logic test 88 causes three actions to occur. First, a new value of P is calculated from the current value of $F_T$. Second, $F_T$ is reset to 0. Third, the clock time t is reset to 0. The computation of P from $F_T$ may proceed in a number of ways, starting from the universal curve in FIG. 12, as described above. In one preferred implementation, we precompute values of P versus $F_T$ and store them in a lookup table so that all the steps shown in FIG. 13 can be implemented at very high speeds in a programmable gate array. If it is desirable to suppress fluctuations in F caused by the small numbers of counts occurring in a short sampling time $\Delta t$, consecutive values of P may also be averaged, either by a running average or by a decaying exponential average of the type described by Warburton and Zhou [WARBURTON 1999B] wherein the $(i+1)^{th}$ average $<P>_{i+1}$ of P is obtained from the $i^{th}$ average $<P>_i$ of P and the $(i+1)^{th}$ value $P_{i+1}$ of P by $$<P>_{i+1}=P_{i+1}/K+<P>_i(K-1)/K, \tag{7}$$

where this may also be carried out in a programmable gate array.

Modeled Results of the Fast Pileup Corrected Running Average Model

Figure 14A:
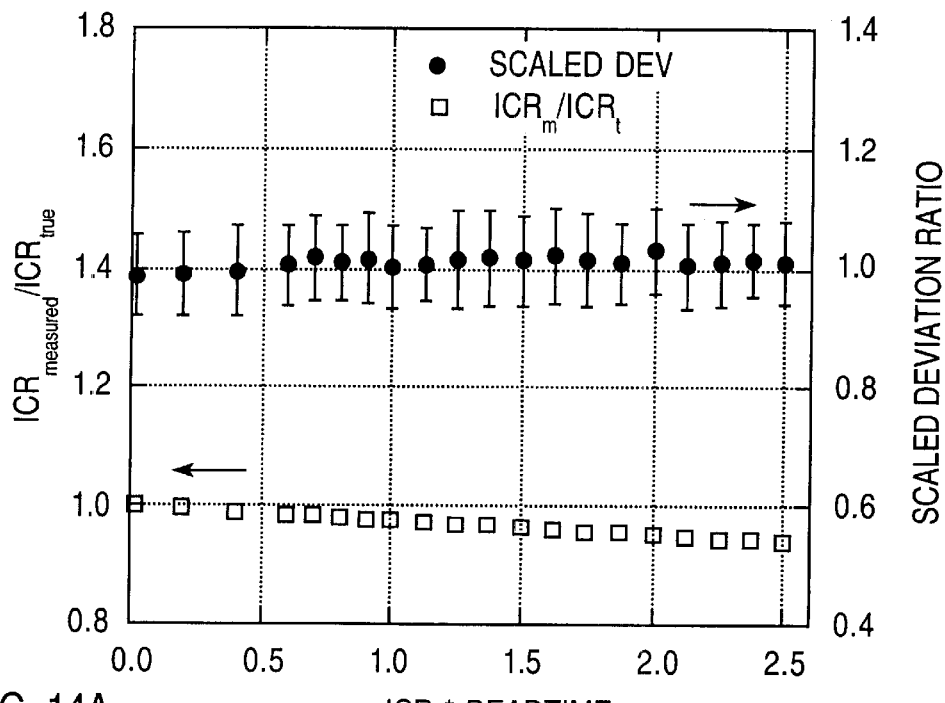
Figure 14B:
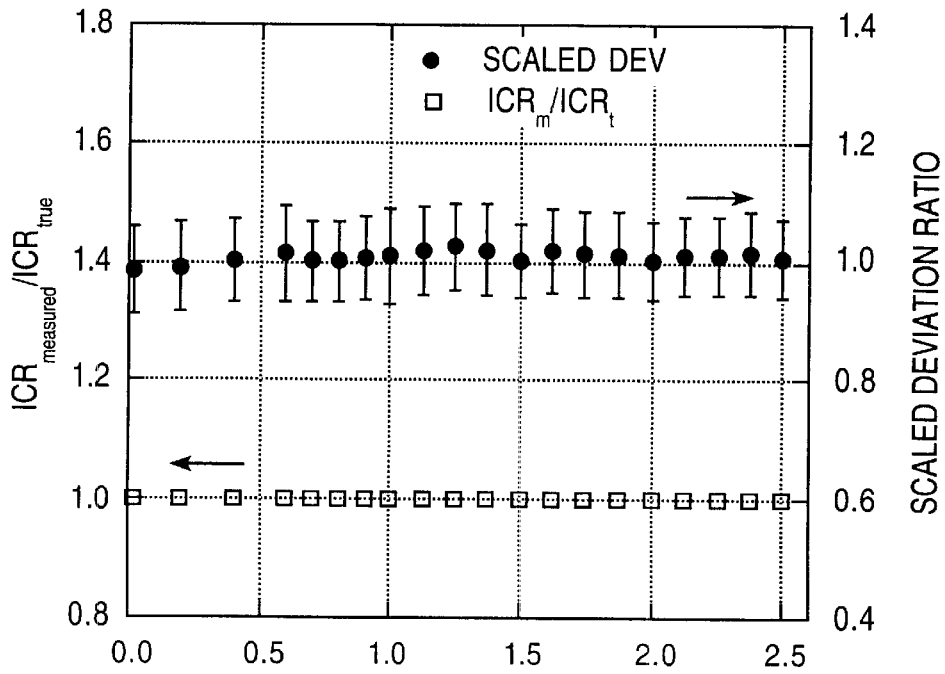
FIG. 14B repeats FIG. 14A when fast pileup corrections are included in the model and are corrected for, per the method outlined in FIG. 13.

FIGS. 14A and 14B show the results obtained from Monte Carlo modeling this method for values of ρ between 0 and 2.5 and M equal to 32. In FIG. 14A there is no fast pileup correction and, while the scaled deviation ratio is just as accurate as in the uncorrected model, we see that there are errors in the measured ICR of up to 5% of the true ICR. However, as shown in FIG. 14B, when the fast pileup correction is implemented, the true input count rate becomes correctly estimated. Therefore, we conclude that implementing fast pileup correction in estimating the counts lost to slow pileup can result in a significant improvement in accuracy at very high count rates where ρ substantially exceeds unity.

It is also worth noting that, having been modeled independently, FIGS. 11, 14A, and 14B provide three independent estimates of the accuracy with which our scaled deviation ratios approach unity. In FIG. 11 the average was 1.004±0.010. In FIGS. 14A and 14B, the averages are 1.010±0.010 and 1.009±0.010, respectively. Thus, our best estimate of the accuracy becomes 1.008±0.010, which is better than 1% and more than accurate enough for estimating standard deviations for curve fitting and other statistical purposes.

Application to Our Other Methods

In the implementation described above, the quantity P added to the fast pulse counter was not an integer value. Since a requirement of our circular averaging method, and an advantage of our bucket averaging method, was that both could be implemented using only integer arithmetic, we cannot simply add in P values as we did in the running average method. In these methods, therefore, we use P as a probability to decide on a pulse by pulse basis whether or not to add in an additional fast pulse. We therefore implement a random number generator to produce evenly distributed values on the interval 0 to 1 and roll it for each found fast pulse. If the value is less than P, then we add an additional fast pulse to the fast pulse counter in the bucket method or store an additional fast pulse in the circular averaging method. We note that if we truly must avoid non-integers anywhere in our computation, we can scale the P values by a constant (e.g., 1024) and then roll random numbers on the interval 0 to 1023.

Other than this modification, the changes required in converting the flow charts for the circular averaging (FIG. 6B) and bucket averaging (FIG. 8) methods to their fast pileup corrected equivalents will simply follow those in going from FIG. 10 to FIG. 13 for the running average method.

4. References

The following are incorporated by reference:
BINGHAM 2001: U.S. Pat. No. 6,327,549, issued Dec. 4, 2001 to Russell D. Bingham, Dale A. Gedcke, Rex C. Trammel, Timothy R. Twomey, and Ronald M. Keyser for "Differential Correction Method and Apparatus".
HARMS 1967: J. Harms, Nuclear Instruments & Methods, 53 (1967) 192. See also: C. F. Masters and L. V. East, IEEE Trans. Nuclear Science, 17 (1970) 383.
JENKINS 1981: "Quantitative X-ray Spectrometry", by Jenkins, R., Gould, R. W., and Gedcke, D. (Marcel Dekker, New York, 1981), Chapter 4, Sections 5 to 8.
KNOLL 1989: "Radiation Detection and Measurement," 2nd Ed. by Glenn F. Knoll (J. Wiley, New York, 1989), Chapter 4, Section VII, "Dead Time" and Chapter 16, Section III, "Pulse Shaping."

UPP 2000: D. L. Upp, R. M. Keyser, D. A. Gedcke, T. R. Twomey, and R. D. Bingham, "An Innovative Method for Dead Time Correction in Nuclear Spectroscopy", Preprint of poster at (MARC V, Honolulu, Hi., Apr. 9–14, 2000).

WARBURTON 1997: U.S. Pat. No. 5,684,850, issued Nov. 4, 1997 to W. K. Warburton and B. Hubbard for "Method and apparatus for digitally based high speed x-ray spectrometer."

WARBURTON 1999A: U.S. Pat. No. 5,870,051, issued Feb. 9, 1999 to W. K. Warburton and B Hubbard for "Method and apparatus for Analog Signal Conditioning for High Speed, Digital X-ray Spectrometer."

WARBURTON 1999B: U.S. Pat. No. 5,873,054, issued Feb. 16, 1999 to W. K. Warburton and Z. Zhou for "Method and apparatus for combinatorial logic signal processor in a digitally based high speed x-ray spectrometer."

WESTPHAL 1984: U.S. Pat. No. 4,476,384, issued Oct. 9, 1984 to Georg P. Westphal for "Method of and system for determining a spectrum of radiation characteristics with full counting-loss compensation".

XIA 1997: X-ray Instrumentation Associates: Application Note 970323-1—"Pileup Inspection and Deadtime in the DXP-4C".

5. CONCLUSION

In the foregoing description of specific embodiments we have shown examples of a technique for extending the Harms method for correcting a spectrum for deadtime losses that not only produces correct results in the presence of time varying input rates but also does so in a manner that also allows the standard deviations in these results to be estimated correctly. We achieved this by, each time a non-piled-up pulse is detected, adding <C> to the corrected output spectrum at the energy of the detected pulse, where <C> is a dynamically adjusted estimate of the average number of detected input counts per detected non-piled-up pulse. All of our methods for estimating <C> produced accurate output spectra. The accuracy with which the standard deviations of the counts in the bins of these output spectra can be estimated, however, varies with the method of estimating <C>. We further demonstrated that, for our implemented methods of estimating <C>, the standard deviation of the counts in each bin of the corrected spectra can then be estimated by scaling the standard deviation of the counts in the same bin of the uncorrected spectra by the ratio of their counts, which is the same method that is commonly used in constant count rate applications where counting times are not livetime extended.

The foregoing description of specific embodiments has been presented for purposes of illustration and description. It is not intended to be exhaustive or to limit the invention to the precise forms described, and obviously, many modifications and variations are possible in light of the above teaching. These embodiments were chosen and described in order to best explain the principles of the invention and its practical application to thereby enable others in the art to best utilize the invention in various embodiments and with such modifications as best suit the invention to the particular uses contemplated.

While the above is a complete description of several specific embodiments of an invention and technique for providing loss free counting in the presence time varying input counting rates, other modifications, alternative constructions, and equivalents may be used. As a first example, although we have separated the spectrometer functions into blocks which separate the spectroscopy amplifier 15 from the MCA or DSP 29, these functions could be combined into a single digital functional element, using, for example, either a large programmable gate array or a fast microprocessor or DSP. Second, while we have shown three different approaches to dynamically estimating <C>, other constructions that perform the same function are clearly possible. Third, while we have presented a table based approach for estimating the probability P of fast pileup occurring, other approaches can be developed. For example, one might build a random pulser with an adjustable output frequency, process these signals and those from the preamplifier using identical digital spectrometers and then adjust the known pulser rate as part of a feedback loop so that the two digital spectrometer output rates track one another over time.

Therefore, the above description should not be taken as limiting the scope of the invention, as defined by the appended claims.

What is claimed is:

1. A method of operating a pulse processing spectrometer to produce an output spectrum of values held in a set of numbered bins, wherein the spectrum, referred to as the corrected spectrum, is corrected for pileup losses, the method comprising:

using a fast channel to detect input pulses;

using pileup inspection circuitry responsive to signals output from the fast channel to determine which detected pulses are piled up and which are not;

using a slow channel to measure the pulses' energies;

capturing energy values from the slow channel for at least some non-piled-up pulses;

associating a bin number with each captured energy value;

producing, from time to time, an estimate <C> of the average ratio of input pulses to non-piled-up pulses; and for each captured energy value, adding <C> to the value held in its associated bin.

2. The method of claim 1, wherein an output spectrum that is a traditional uncorrected output spectrum of values held in an additional set of numbered bins is also produced by, for each captured energy value, additionally adding the value 1 to the value held in the bin in the additional set.

3. The method of claim 2 wherein:

the standard deviation $\sigma_{ci}$ of the counts $N_{ci}$ in the $i^{th}$ bin of said corrected output spectrum is estimated according to the equation $\sigma_{ci} = N_{ci}/\text{sqrt}(N_{ui})$ where $N_{ui}$ is the number of counts in the same $i^{th}$ bin of said uncorrected spectrum.

4. The method of claim 1 wherein said estimate <C> is corrected for pulses lost due to pileup in said fast channel by:

measuring the output counting rate $OCR_{fm}$ of detected pulses in said fast channel;

using said measured $OCR_{fm}$ to estimate the probability P that a given detected pulse in said fast channel is piled up; and in producing estimates of the average ratio of input pulses to non-piled-up pulses, scaling the numbers of detected input pulses by (1+P).

5. The method of claim 4 wherein the scaling is carried out by:

using a counter to record an estimated number of input pulses; and adding (1+P) to the counter each time an input pulse is detected in the fast channel.

6. The method of claim 4 wherein the scaling is carried out by:
   using a counter to record an estimated number of input pulses; and,
   each time an input pulse is detected in the fast channel generating a random number S using a method that produces uniform probabilities between 0 and 1;
   if S is greater than or equal to P, adding 1 to the counter; else
   if S is less than P, adding 2 to the counter.

7. The method of claim 6 wherein, to simplify the generation of S and its comparison to P:
   P is multiplied by a constant K; and
   S is generated using a random number generator that produces uniform probabilities between 0 and K.

8. The method of claim 4 wherein said probability P is estimated from said measured $OCR_{fm}$ by:
   first creating a table of values of P versus X in terms of the parameter $\Delta$, where P and X are given by the equations:

$$P = \exp(\Delta) - 1,$$

and $$X = \tau_{df} \times OCR_{fm} = \Delta \exp(-\Delta);$$

and then, for a known value of the fast channel dead time $\tau_{df}$ and the measured value $OCR_{fm}$, computing X and using the table to produce the estimated probability P.

9. The method of claim 8 wherein the estimation of the probability P from said table is simplified by, for a particular value of the fast channel dead time $\tau_{df}$, and a fixed time $\Delta t$ of measuring $OCR_{fm}$, rescaling X by $\Delta t / \tau_{df}$ to produce a table of values of P versus $N_{fm}$, the number of fast counts detected in the fast channel in the time interval $\Delta t$.

10. The method of claim 1 wherein said estimate of <C> is an average formed by:
    counting, for a sequence of M non-piled-up pulses, the number $F_i$ of pulses detected in said fast channel for each member i of said sequence; and
    forming <C> as the average of the $F_i$ sums according to $$\langle C \rangle = \sum_{i=1}^{M} F_i / M.$$

11. The method of claim 10 wherein said estimate of <C> is a running average $\langle C \rangle_i$ formed for each non-piled-up pulse i by adjusting the value $\langle C \rangle_{i-1}$ formed for the previous non-piled-up pulse according to the equation:

$$\langle C \rangle_i = \langle C \rangle_{i-1} + (F_i - F_{i-M})/M.$$

12. The method of claim 11 wherein:
    M is a power of 2, expressible as $M = 2^L$, where L is an integer; and
    the division $(F_i - F_{i-M})/M$ is carried out digitally by shifting the binary representation of $(F_i - F_{i-M})$ right by L bits.

13. The method of claim 11 wherein correction is made for pulses lost to pileup in the fast channel when forming the sum $N_i$ of pulses detected in the fast channel for the $i^{th}$ non-piled-up pulse by:
    adding 1+P to the sum $F_i$ each time a pulse is detected in the fast channel,
    where P is the probability that a pulse in the fast channel is piled up.

14. The method of claim 11 wherein the division by M is omitted each time $\langle C \rangle_i$ is formed from $\langle C \rangle_{i-1}$ and, instead, is carried out once per bin in the corrected spectrum after data collection is complete.

15. The method of claim 1 wherein said estimate of <C> is a bucket average formed, for a sequence of M non-piled-up pulses, by:
    adding 1 to a pulse count F each time a pulse is detected in said fast channel;
    subtracting the current value of <C> from the pulse count F each time a non-piled-up pulse is binned to the corrected spectrum; and
    at the end of the sequence of M non-piled-up pulses, adding the quotient of F/M, rounded to the nearest integer, to <C>.

16. The method of claim 15 wherein:
    M is a power of 2, expressible as $M = 2^L$, and
    the division F/M is carried out digitally by shifting the binary representation of F right by L bits.

17. The method of claim 15 wherein correction is made for pulses lost to pileup in the fast channel by adding 1+P to said pulse count F for each pulse detected in said fast channel where P is the probability that a pulse in the fast channel is piled up.

18. The method of claim 15 wherein correction is made for pulses lost to pileup in the fast channel by:
    generating, each time 1 is to be added to said fast counter F, a random number S using a method that produces uniform probabilities between 0 and 1; and
    if S is less than P, adding 2 to the pulse count F, where P is the probability that a pulse in the fast channel is piled up.

19. The method of claim 1 wherein said estimate of <C> is a circular average formed by:
    creating a circular buffer memory of length M that is addressable by two pointers—a good pulse pointer $P_G$ and a fast pulse pointer $P_F$—whose arithmetic is computed modulo M; and
    each time a pulse is detected in the fast channel:
        adding 1 to the value $C_K$ stored at location K pointed to by the fast pulse pointer $P_F$; and
        then incrementing $P_F$ by 1 modulo M; and
    each time a non-piled-up pulse is to be binned to the corrected spectrum:
        using the value $C_L$ stored at the location L pointed to by the good pulse pointer $P_G$ as the value of <C> to be binned in the output spectrum;
        setting the value $C_L$ stored at said location L to zero; and
        incrementing $P_G$ by 1 modulo M.

20. The method of claim 19 wherein correction is made for pulses lost to pileup in the fast channel by:
    each time 1 is added to said value $C_K$ stored at location K pointed to by the fast pulse pointer $P_F$, generating a random number S using a method that produces uniform probabilities between 0 and 1; and
    if S is less than P, additionally adding 1 to $C_K$, where P is the probability that a pulse in the fast channel is piled up.

21. In a pulse processing spectrometer that uses a fast channel to detect input pulses and measure the time intervals between them, a slow channel to measure the pulses' energies, pileup inspection circuitry responsive to fast channel outputs that causes pulse energy values to be captured from the slow channel only for non-piled-up pulses, and binning means to produce an output spectrum of said captured energy values, apparatus for generating a spectrum, referred to as the corrected spectrum, that is corrected for pileup losses, the apparatus comprising:

means for producing, from time to time, an estimate <C> of the average ratio of the number of input pulses detected in said fast channel per non-piled-up pulse whose captured energy value is to be binned in said corrected spectrum; and means, responsive to the detection of a given non-piled-up pulse, for adding the value <C> to said corrected spectrum in the bin dictated by the given pulse's captured energy value.

22. The apparatus of claim 21, further comprising:
means, for each said non-piled-up pulse, for additionally adding the value 1 to a second, uncorrected output spectrum in the same bin as the value <C> was added to said corrected spectrum, thereby producing a traditional, uncorrected spectrum.

23. The apparatus of claim 21, further including means, for each bin i in said corrected spectrum, for estimating the standard deviation $\sigma_{ci}$ of the counts $N_{ci}$ in said bin i, said means comprising:

means for computing $\sigma_{ci}=N_{ci}/\sqrt{N_{ui}}$, where $N_{ui}$ is the number of counts in the same $i^{th}$ bin in said uncorrected spectrum.

24. The apparatus of claim 21, further including means for correcting said estimate <C> for pulses lost due to pileup in said fast channel, said means comprising:

means for measuring the output counting rate $OCR_{fm}$ of detected pulses in said fast channel;

means for estimating the probability P that a given detected pulse in said fast channel is piled up, using said measured $OCR_{fm}$; and in said means for producing <C>, additional means for including the probability P to correct <C> for said pileup losses in said fast channel.

25. The apparatus of claim 24 wherein said additional means include means that, whenever said means for producing <C> adds 1 to a counter used to represent the detection of a pulse in the fast channel, additionally adding P.

26. The apparatus of claim 24 wherein said additional means for correcting <C> include means that, whenever said means for producing <C> adds 1 count to a counter used to represent the detection of a pulse in the fast channel, further generates a random number S using a generator that produces uniform probabilities between 0 and 1;
compares S to P; and
if S is less than P, adds an additional count to said counter.

27. The apparatus of claim 24 wherein said means for estimating the probability P include:

a table of values of P versus X, where $X=\tau_{df} \times OCR_{fm}$;
means, given a known value of the fast channel dead time $\tau_{df}$ and the measured value $OCR_{fm}$, for computing X; and
means for extracting a value of P from said table for a given value of X;
where said table of values of P versus X is generated in terms of a parameter $\Delta$, with P and X being given by the equations:

$$P=\exp(\Delta)-1,$$

and $$X=\Delta \exp(-\Delta).$$

28. The apparatus of claim 27 wherein said means for measuring $OCR_{fm}$ comprises means for recording $N_{fm}$, the number of fast counts detected in the fast channel in a fixed time interval $\Delta t$;

said table is replaced by a table of values of P versus $N_{fm}=X\Delta t/\tau_{df}$, generated by the equations:

$$P=\exp(\Delta)-1,$$

and $$N_{fm}=\Delta \exp(-\Delta)(\Delta t/\tau_{df});$$

and said extracting means are modified to extract a value of P from said table for a given value of $N_{fm}$.

29. The apparatus of claim 21 wherein said means for producing an estimate <C> include:

a counter for counting the number $N_i$ of pulses detected in said fast channel for each member i of a sequence of M non-piled-up pulses; and an adder and a divider connected to form <C> according to the equation $$\langle C \rangle = \sum_{i=1}^{M} N_i / M.$$

30. The apparatus of claim 21 wherein said means for producing an estimate <C> compute <C> for each non-piled-up pulse as a running average of length M, the means including:

an adder that forms the sum $N_i$ of pulses detected in said fast channel for each non-piled-up pulse by adding 1 each time a pulse is detected in said fast channel;

storage means for storing at least the M previous values of $N_i$; and computing means for computing $\langle C \rangle_i$ for the $i^{th}$ non-piled-up pulse from $\langle C \rangle_{i-1}$ according to the equation:

$$\langle C \rangle_i = \langle C \rangle_{i-1} + (N_i - N_{i-M})/M.$$

31. The apparatus of claim 30 that also corrects for pulses lost to pileup in the fast channel by adding 1+P to the sum $N_i$ each time a pulse is detected in said fast channel, where P is the probability that a pulse in the fast channel is piled up.

32. The apparatus of claim 21 wherein said means for producing an estimate <C> includes:

means for counting a sequence of M non-piled-up pulses;
means for storing a pulse count F and the current estimate of <C>;
an adder that adds 1 count to F for each pulse detected in said fast channel;
a subtracter that subtracts the current value of <C> from F each time a non-piled-up pulse is binned to the corrected spectrum; and
means, each time a sequence of M non-piled-up pulses is counted, for adding the quotient of F/M, rounded to the nearest integer, to the current estimate of <C>.

33. The apparatus of claim 32, further including means for correcting <C> for pulses lost to pileup in the fast channel by adding 1+P to the pulse count F each time a pulse is detected in said fast channel, where P is the probability that a pulse in the fast channel is piled up.

34. The apparatus of claim 32, further including means for correcting <C> for pulses lost to pileup in the fast channel by, each time said adder adds 1 count to F:

generating a random number S using a random number generator that produces a uniform distribution on the interval 0 to 1;

using a comparator to compare S to P; and if S is less than P, adding an additional count to F.

35. The apparatus of claim 21 wherein said means for producing an estimate <C> includes:

a circular buffer memory of length M addressable by two pointers—a good pulse pointer $P_G$ and a fast pulse pointer $P_F$—whose arithmetic is computed modulo M;

means, each time a pulse is detected in the fast channel, for adding 1 to the value $C_K$ stored at location K pointed to by the fast pulse pointer $P_F$, and then incrementing $P_F$ by 1 modulo M; and means, each time a non-piled-up pulse is to be binned to the output spectrum, for using the value $C_L$ stored at the location L pointed to by the good pulse pointer $P_G$ as the value of <C> to be binned in the output spectrum;

setting the value $C_L$ stored at said location L to zero; and incrementing $P_G$ by 1 modulo M.

36. The apparatus of claim 35 that, further including means for correcting <C> for pulses lost to pileup in the fast channel by, each time 1 is added to the value $C_K$ stored at location K pointed to by the fast pulse pointer $P_F$:

generating a random number S using a random number generator that produces a uniform distribution on the interval 0 to 1;

using a comparator to compare S to P; and if S is less than P, adding an additional count to $C_K$.

* * * * *